United States Patent
Anderson et al.

(10) Patent No.: US 11,412,928 B2
(45) Date of Patent: Aug. 16, 2022

(54) SYSTEMS AND METHODS FOR IMPROVED OPHTHALMIC IMAGING

(71) Applicants: Carl Zeiss Meditec, Inc., Dublin, CA (US); Carl Zeiss Meditec AG, Jena (DE)

(72) Inventors: Gregory Anderson, Dublin, CA (US); Muzammil Arain, Dublin, CA (US); Keith Brock, Dublin, CA (US); Scott Chang, Dublin, CA (US); Matthew J. Everett, Livermore, CA (US); Zubir Khan, Dublin, CA (US); Archana Kolli, Dublin, CA (US); Priya Kulkarni, Dublin, CA (US); Benjamin Kwok, Dublin, CA (US); Conor Leahy, Dublin, CA (US); Gary Lee, Dublin, CA (US); Jennifer Luu, Dublin, CA (US); Pranav Malvania, Dublin, CA (US); David Nolan, Dublin, CA (US); Keith O'Hara, Pleasanton, CA (US); Sunny Virmani, Dublin, CA (US); Richard Orlowski, Dublin, CA (US)

(73) Assignees: Carl Zeiss Meditec, Inc., Dublin, CA (US); Carl Zeiss Meditec AG, Jena (DE)

( * ) Notice: Subject to any disclaimer, the term of this patent is extended or adjusted under 35 U.S.C. 154(b) by 166 days.

(21) Appl. No.: 16/633,139

(22) PCT Filed: Aug. 10, 2018

(86) PCT No.: PCT/EP2018/071744
§ 371 (c)(1),
(2) Date: Jan. 22, 2020

(87) PCT Pub. No.: WO2019/030375
PCT Pub. Date: Feb. 14, 2019

(65) Prior Publication Data
US 2020/0196863 A1 Jun. 25, 2020

Related U.S. Application Data

(60) Provisional application No. 62/544,056, filed on Aug. 11, 2017.

(51) Int. Cl.
A61B 3/15 (2006.01)
A61B 3/00 (2006.01)
(Continued)

(52) U.S. Cl.
CPC ............ A61B 3/152 (2013.01); A61B 3/0008 (2013.01); A61B 3/0025 (2013.01);
(Continued)

(58) Field of Classification Search
CPC ..... A61B 3/152; A61B 3/0008; A61B 3/0025; A61B 3/0033; A61B 3/0058;
(Continued)

(56) References Cited

U.S. PATENT DOCUMENTS

| 4,170,398 A | 10/1979 | Koester |
| 4,732,466 A | 3/1988 | Humphrey |

(Continued)

FOREIGN PATENT DOCUMENTS

| EP | 2702931 A2 | 3/2014 |
| EP | 2932888 A1 | 10/2015 |

(Continued)

OTHER PUBLICATIONS

Blazkiewicz et al., (2005). "Signal-to-noise ratio study of full-field Fourier-domain optical coherence tomography," Applied Optics, 44:7722-9.

(Continued)

*Primary Examiner* — Mohammed A Hasan
(74) *Attorney, Agent, or Firm* — Morrison & Foerster LLP

(57) ABSTRACT

An ophthalmic imaging system has a specialized graphical user interface GUI to convey information for manually
(Continued)

adjusting control inputs to bring an eye into alignment with the device. The GUI provides additional information such as laterality, visual alignment overlay aids, and live video feeds. The system further applies automatic gain control to fundus images, synchronizes itself with other ophthalmic systems on a computer network, and provides an optimized image load and display system.

20 Claims, 19 Drawing Sheets

(51) Int. Cl.
 A61B 3/10 (2006.01)
 A61B 3/12 (2006.01)
(52) U.S. Cl.
 CPC .......... *A61B 3/0033* (2013.01); *A61B 3/0058* (2013.01); *A61B 3/0075* (2013.01); *A61B 3/0091* (2013.01); *A61B 3/102* (2013.01); *A61B 3/1216* (2013.01)
(58) Field of Classification Search
 CPC ..... A61B 3/0075; A61B 3/0091; A61B 3/102; A61B 3/1216; A61B 3/1025; A61B 3/0083; A61B 3/0041
 USPC .......................................................... 351/208
 See application file for complete search history.

(56) References Cited

U.S. PATENT DOCUMENTS

| | | | |
|---|---|---|---|
| 6,322,216 B1 | 11/2001 | Yee et al. | |
| 7,301,644 B2 | 11/2007 | Knighton et al. | |
| 8,223,143 B2 | 7/2012 | Dastmalchi et al. | |
| 8,224,050 B2 | 7/2012 | Doering et al. | |
| 8,332,016 B2 | 12/2012 | Stetson | |
| 9,778,021 B2 | 10/2017 | Bagherinia | |
| 2003/0076353 A1* | 4/2003 | Blackstock | G06F 3/0481 715/751 |
| 2007/0076958 A1 | 4/2007 | Venkatesh | |
| 2009/0251665 A1 | 10/2009 | Hara | |
| 2010/0094262 A1* | 4/2010 | Tripathi | A61B 3/0058 606/1 |
| 2010/0296057 A1 | 11/2010 | Nagashio et al. | |
| 2011/0234977 A1 | 9/2011 | Verdooner | |
| 2012/0059236 A1 | 3/2012 | Pinezi | |
| 2013/0176532 A1 | 7/2013 | Sharma et al. | |
| 2014/0063456 A1 | 3/2014 | Zhou et al. | |
| 2014/0128852 A1* | 5/2014 | Gooding | A61F 9/008 606/4 |
| 2014/0232987 A1 | 8/2014 | Westphal et al. | |
| 2014/0320810 A1* | 10/2014 | Fukuma | A61B 3/102 351/206 |
| 2014/0343541 A1* | 11/2014 | Scott | A61F 9/008 606/4 |
| 2015/0131050 A1 | 5/2015 | Bublitz et al. | |
| 2015/0265147 A1* | 9/2015 | Gooding | A61B 3/102 600/426 |
| 2016/0095752 A1* | 4/2016 | Srinivasan | A61F 9/00827 606/6 |
| 2016/0161404 A1* | 6/2016 | Marshall | C12Q 1/04 435/34 |
| 2016/0227999 A1 | 8/2016 | An et al. | |
| 2017/0032564 A1 | 2/2017 | Dastmalchi et al. | |
| 2017/0189233 A1* | 7/2017 | Dewey | A61F 9/00825 |
| 2017/0316565 A1 | 11/2017 | Leahy et al. | |

FOREIGN PATENT DOCUMENTS

| | | |
|---|---|---|
| WO | WO-1999005988 A2 | 2/1999 |
| WO | WO-2012059236 A1 | 5/2012 |
| WO | WO-2015189174 A2 | 12/2015 |
| WO | WO-2016124644 A1 | 8/2016 |
| WO | WO-2017218738 A1 | 12/2017 |
| WO | WO-2018178269 A1 | 10/2018 |
| WO | WO-2019030375 A2 | 2/2019 |

OTHER PUBLICATIONS

Bonin et al., (2010). "In vivo Fourier-domain full-field OCT of the human retina with 1.5 million A-lines/s," Optics Letters, 35:3432-3434.
Brown et al., (2003). "Recognizing Panoramas," University of British Columbia, Department of Computer Science, 8 pages.
Brown et al., (2007). "Automatic Panoramic Image Stitching using Invariant Features," University of British Columbia, Department of Computer Science, 16 pages.
Fercher et al., (1988). "Eye-length measurement by interferometry with partially coherent light," Optics Letters, 13(3):186-188.
Grajciar et al., (2005). "Parallel Fourier domain optical coherence tomography for in vivo measurement of the human eye," Optics Express, 13:1131-7.
Hiratsuka et al., (1998). "Simultaneous measurements of three-dimensional reflectivity distributions in scattering media based on optical frequency-domain reflectometry," Optics Letters, 23:1420-1422.
Huang et al., (1991). "Optical Coherence Tomography," Science, 254:1178-1181, 12 pages.
International Search Report and Written Opinion received for International Patent Application No. PCT/EP2018/071744, dated Mar. 20, 2019, 18 pages.
Invitation to Pay Additional Fees received for International Patent Application No. PCT/EP2018/071744, dated Dec. 10, 2018, 14 pages.
Klein et al., (2013). "Joint aperture detection for speckle reduction and increased collection efficiency in ophthalmic MHz OCT," Biomedical Optics Express, 4:619-634.
Kwatra et al., (2003). "Graphcut Textures: Image and Video Synthesis Using Graph Cuts," available online at <https://www.cc.gatech.edu/cpl/projects/graphcuttextures/gc-final.pdf>, 10 pages.
Laraqui et al., (2017). "Image Mosaicing using Voronoi diagrams," Multimedia Tools and Applications, 76:8803-8829.
Lee et al., (2008). "Line-Field Optical Coherence Tomography Using Frequency-Sweeping Source," IEE Journal of Selected Topics in Quantum Electronics, 12:50-55.
Li et al., (2011). "Automatic montage of SD-OCT datasets," Optics Express, 19:26239-26248.
Mujat et al., (2009). "Swept-source parallel OCT," SPIE, 7168:E1-E8.
MySQL, (2019). "21.6.10 NBD Cluster Replication: Multi-Master and Circular Replication," MySQL 5.7 Reference Manual, 8 pages.
Nakamura et al., (2007). "High-speed three-dimensional human retinal imaging by line-field spectral domain optical coherence tomography," Optics Express, 15:7103-7116.
Nankivil et al., (2014). "Coherence revival multiplexed, buffered swept source optical coherence tomography: 400 kHz imaging with a 100 kHz source," Optics Letters, 39:3740-3743.
OpenCV, (2019). "Seam Estimation," available online at <https://docs.huihoo.com/opencv/2.4-documentation/modules/stitching/doc/seam_estimation.html#detail-seamfinder>, 4 pages.
Potsaid et al., (2010). "Ultrahigh speed 1050nm swept source / Fourier domain OCT retinal and anterior segment imaging at 100,000 to 400,000 axial scans per second," Optics Express, 18:20029-48.
Povazay et al., (2006). "Full-field time-encoded frequency-domain optical coherence tomography," Optics Express, 14:7661-9.
Shi et al., (1994). "Good Features to Track," IEE Conference on Computer Vision and Pattern Recognition, 8 pages.
Thevenaz et al., (2007). "User-Friendly Semiautomated Assembly of Accurate Image Mosaics in Microscopy," Microscopy research and technique, 70:135-146.
Wieser et al., (2010). "Multi-Megahertz OCT: High quality 3D imaging at 20 million A-scans and 4.5 GVoxels per second," Optics Express, 18:14685-14704.

(56) References Cited

OTHER PUBLICATIONS

Zhang et al., (2015). "Minimizing projection artifacts for accurate presentation of choroidal neovascularization in OCT micro-angiography," Biomedical Optics Express, 6:4130-4143.

Zhang et al., (2016). "Projection-resolved optical coherence tomographic angiography," Biomedical Optics Express, 7:816-828.

Zuluaga et al., (1999). "Spatially resolved spectral interferometry for determination of subsurface structure," Optics Letters, 24:519-521.

* cited by examiner

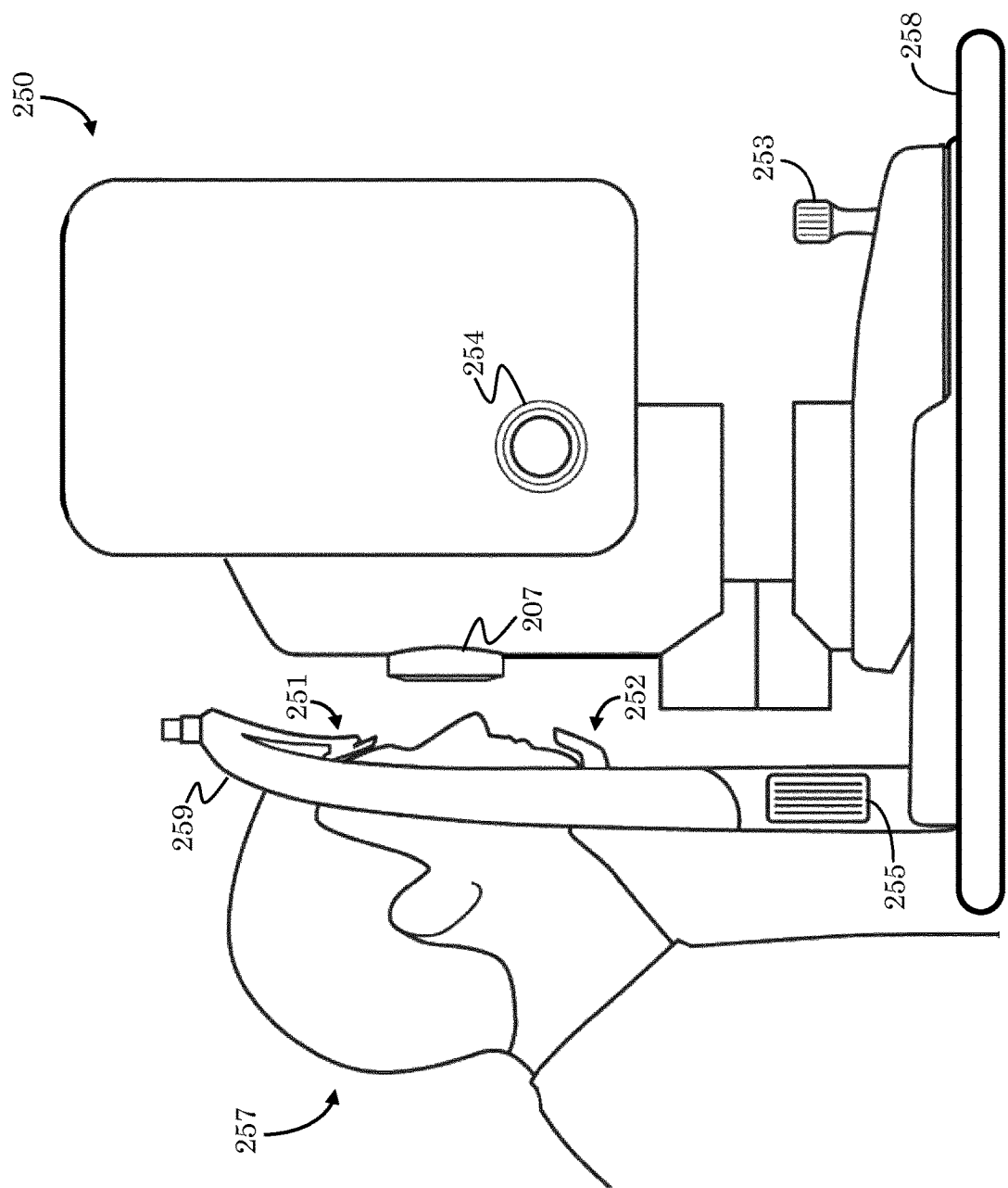

FIG. 3a

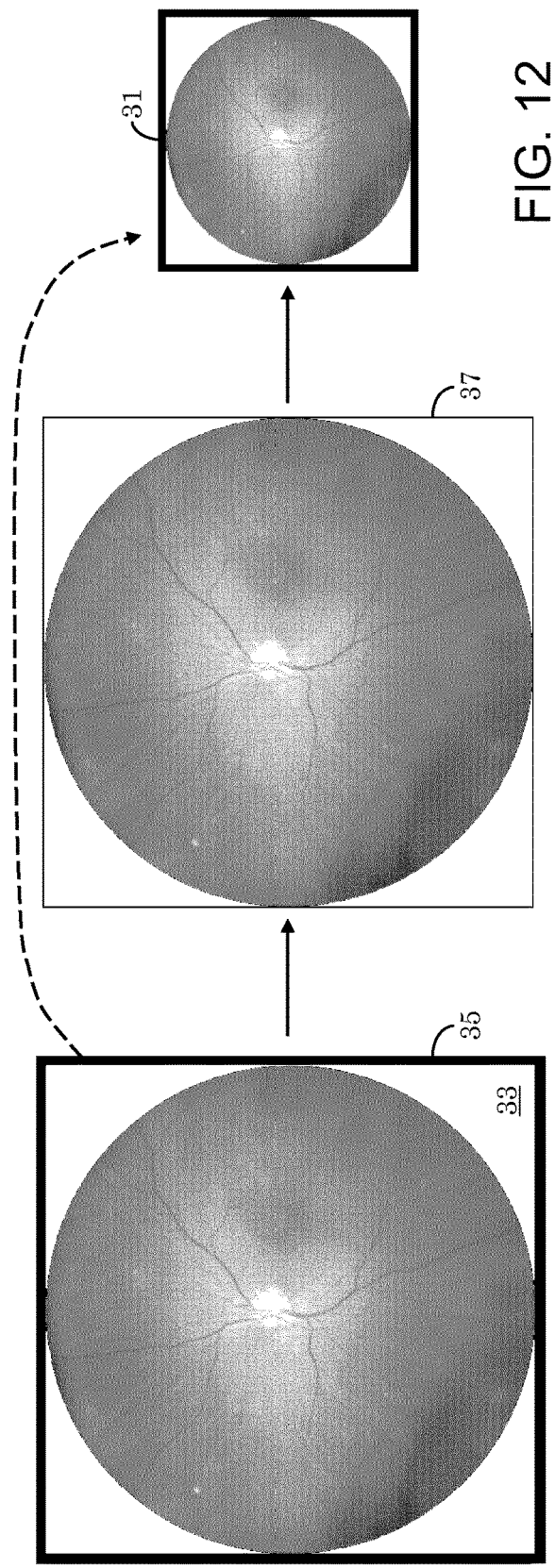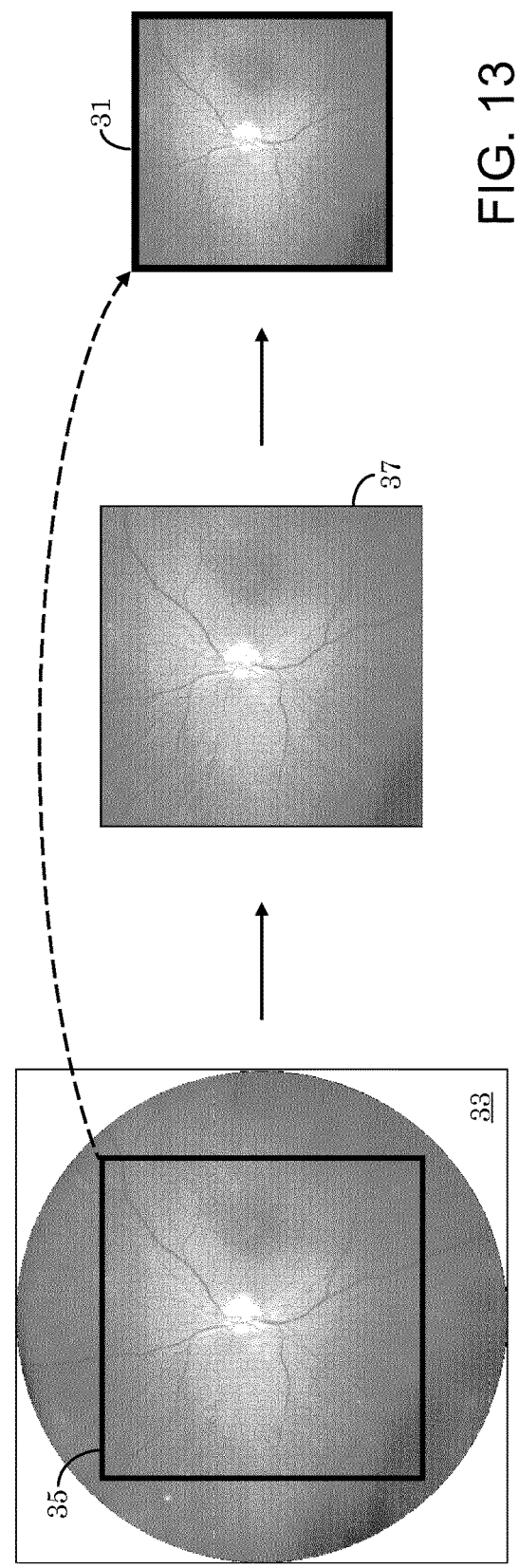

SYSTEMS AND METHODS FOR IMPROVED OPHTHALMIC IMAGING

PRIORITY

This application is a National Phase application under 35 U.S.C. § 371 of International Application No. PCT/EP2018/071744, filed Aug. 10, 2018, which claims priority to U.S. Provisional Application Ser. No. 62/544,056 filed Aug. 11, 2017, the contents of which are hereby incorporated by reference in their entirety.

FIELD OF INVENTION

The present invention is generally directed to the field of ophthalmic imaging systems. More specifically, it is directed to techniques for facilitating user operation of ophthalmic imaging system.

BACKGROUND

There are various type of ophthalmic examination systems, including ophthalmoscopes, Optical Coherence Tomography (OCT), and other ophthalmic imaging systems. One example of an ophthalmic imaging is slit-Scanning or Broad-Line fundus imaging (see for example U.S. Pat. Nos. 4,170,398, 4,732,466, PCT Publication No. 2012059236, US Patent Application No. 2014/0232987, and US Patent Publication No. 2015/0131050, the contents of all of which are hereby incorporated by reference), which is a promising technique for achieving high resolution in vivo imaging of the human retina. The imaging approach is a hybrid between confocal and widefield imaging systems. By illuminating a narrow strip of the retina while scanning, the illumination stays out of the viewing path, which enables a clearer view of much more of the retina than the annular ring illumination used in traditional fundus cameras.

To obtain a good image, it is desirable for the illuminating strip to pass unabated through the pupil, and reach the fundus, of an eye. This requires careful alignment of the eye with the ophthalmic imager (or other ophthalmic examination system). Consequently, much training is generally needed to achieve a high level of competency in using such systems.

It is an object of the present invention to provide tools to facilitate the alignment of an eye with an ophthalmic examination system.

It is another object of the present invention to provide various methods of conveying ophthalmic-related information to a user of an ophthalmic examination system.

It is a further object of the present invention to provide a method/device/system for synchronizing ophthalmic-related information across multiple ophthalmic examination system.

It is a further object of the present invention to provide a system and method for optimizing file management within an ophthalmic examination system.

SUMMARY OF INVENTION

The above objects are met in a system and method for controlling an ophthalmic imaging system, and a graphical user interface (GUI) for interfacing with the ophthalmic imaging system.

Herein is presented a system and method that displays a graphical user interface (GUI) on a computer screen. The GUI includes an information-display region, which may be divided into multiple sections and/or viewports. In some embodiments, the information-display region displays a live feed (e.g., preview video) from one or more cameras of an ophthalmic imaging system, e.g., while it is imaging an eye. The ophthalmic imaging system may be, for example, a fundus imager, an optical coherence tomography (OCT), or a combination of both. To aid with aligning the system with the eye, an alignment indicator specifying a target view of the eye when in alignment may be overlaid on the information-display region. Additionally, the information-display region may identify a manual controller of the ophthalmic imaging system operable by a user to improve alignment between the camera and the eye. This helps the human operator to more quickly identify the control needed to bring the eye into alignment.

The system may identify the manual control by use of a graphic representation of the manual controller. Additionally, the system may provide information regarding how to manipulate the manual controller to improve alignment. This information may be provided by use of an animation depicting the manipulation, arrows conveying movement of the manual controller, and/or textual instructions. Optionally, the information may also be conveyed audibly.

The alignment indicator may take various forms. For example, it may be a partially transparent bar indicating a minimum height of the pupil of the eye when aligned, two lines indicating the minimum height of the pupil of the eye when aligned, crosshairs specifying a central location for the eye when aligned, and an oval whose outline specifies a minimum size of the pupil of the eye when aligned. The determination of the minimum height or minimum size displayed may be based on eye measurements at least partially determined from the live feed.

To further aid an operator, the system may automatically activate an image capture sequence in response to determining that the eye is aligned with the system, based at least in part of on a comparison of the alignment indicator and the live feed. As mentioned above, the system may determine the size of the eye's pupil based on the live feed. In this case, the system may optionally, automatically select one of multiple imaging modalities based on the determined size. Examples of different modalities include a mydriatic imaging mode and a non-mydriatic imaging mode.

To assure patient privacy, the present system may also provide a simple method for quickly hiding patient information on a computer screen. For example, the GUI may include a privacy icon depicting a computer display with an attached window shade that is at least partly opened and the system may respond to user selection of this privacy icon (e.g., by use of an input device) by removing from view information currently displayed in the information-display region. Optionally, the GUI may respond to user-selection of the privacy icon by at least partially closing its window shade, which may include a depiction of the window shade moving over the computer display of the privacy icon. Additionally, the removing from view of information in the information-display region may include an overlay that travels over, and covers, the information-display region, where the traveling of the overlay mimics the closing of the window shade on the privacy icon.

Sometimes when examining a patient's ophthalmic image, a doctor may make annotations or measurements of various features. Since a patient may have multiple images, the present system further provides a method to quickly replicate notes/measurements on one image to another. For example, the GUI may include a source icon and a destination icon. The system may associate at least a user-selected source file with the source icon, and associate at least one user-selected destination file with the destination icon. Then, in response to a user input by use of an input device, the system copies user-made annotations on the source file associated with the source icon to the destination files associated with the destination icon. It is to be understood that the source file(s) and destination file(s) may be image files. In this case, user-made annotations on the source image file define an area of the source image file, and the user-made annotations are copied to a matching area of the destination image file.

The GUI may include a laterality icon that specifies whether the ophthalmic information displayed in the information-display region is from a left eye or right eye of a patient, and indicates whether the specified laterality is from the patient's point of view or from a doctor's point of view. Optionally, user selection of the laterality icon toggles the laterality between the doctor's and the patient's point of view.

The information-display region may also display a montaged image comprised of at least two fundus images. The GUI may include a montage icon depicting the outer perimeter shape of the montaged image. The montage icon may further be divided into sectors, with each sector corresponding to a separate one of the fundus images, and indicating the boundaries of the fundus images in the montaged image.

The system may include a fixation light to convey a fixation direction to a patient. In this case, the GUI may include a blink icon associated with the fixation light, and user selection of the blink icon may cause the fixation light to temporarily strobe.

An issue that further complicates the imaging of the retina, is that different eyes have differently pigmented retinas. This may result in in a captured image appearing saturated (e.g., too bright). The present system therefore provides a mechanism/method for automatically controlling the gain of its retina (or fundus) camera. This permits it to, for example, lower the gain for lightly pigmented retinas, and increase the gain for darkly pigmented retinas. This mechanism captures an image of the fundus of the eye, and then determines whether at least a portion of a retina (or other target subject to be imaged) is likely within the captured imaged. The system then designates the captured image as valid if the retina is determined to be within the captured image, and designates the captured image as not valid if the retina is determined to not be within the captured image. This avoids taking into consideration images taken while the patient blinked or moved or otherwise went out of alignment with the system. The system then evaluates the illumination of a predefined number of consecutive valid images, and adjusts the camera gain value (e.g., of the retina/fundus camera) based at least in part on the evaluated illumination.

Determining whether the captured image (e.g., the retina image) is valid may make use of another camera and/or another image. For example, an iris camera may take pictures of the exterior of the eye to determine when the patient blinked, moved, or was out of alignment. The results of this iris camera may inform the system as to when to designate a captured fundus image as not valid, or suspect. For example, if the captured fundus image is termed a first image, the determination of whether at least a portion of the retina is within the first image may include capturing a second image excluding the fundus (e.g., an image of the exterior of the eye). The presence of the retina in the first image may be based at least in part on the second image, which identifies eye blinks, movements, misalignments, or other factors that may interfere with the fundus camera capturing a good image of the retina.

The information-display region may also display a selection of images from which the user may select. In response to user selection of a target image within the selection of images, the system may: identify acquisition parameters of the target image including at least one of a fixation angle, image capture modality, diagnosed pathology, and patient name; access an image database and identify at least one secondary image having acquisition parameters matching the identified acquisition parameters of the target image; and display the at least one secondary image.

The information-display region may also display a patient record access portal having a plurality of user-selectable options, where at least one user-selectable option is a target option associated with one or more images. For example, the user-selectable option may be a patient name, a time frame during which images were taken, a list (text and/or thumbnails) of images to select from, etc. In response to a user selection of the target option, the system may initiate loading of the images associated with the target option irrespective of whether the user has elected to view any image associated with the target option. This effectively provides a pre-fetching operation. To reduce memory requirements, for each loaded imaged, the system create a plurality of copies of the loaded image (optionally, the originally loaded image may be discarded). The system may also apply image correction and other preprocessing routines to the copies of the loaded image. The copies are of decreasing resolution and may be stored in an image cache. The system may then respond to the user electing to view a specific image associated with the target option within a viewport of first resolution by displaying, from the image cache, a lower resolution copy of the specific image whose lower resolution is closest to, but higher than, the first resolution of the viewport.

Responding to the user electing to view the specific image may also include cropping an area of the copy to be displayed, where the cropped area corresponds to the viewport, e.g., the cropped area is of similar shape and location. The cropped area may be resized to match the resolution of the viewport. The resized cropped area is then displayed in the viewport.

In this approach, the system may respond to the viewport specifying a zoom selection by, if the resolution of the currently displayed copy is greater than the zoom selection of the viewport, cropping the currently displayed copy to display the zoom selection without applying a scaling factor to the copy, else replacing the currently displayed copy with another copy whose resolution is closest to, but greater than, the resolution of the zoom selection of the viewport.

Also in this approach, the system may respond to a panning action of the viewport by defining a cropped area of the currently displayed copy. The cropped area may be larger than the viewport and the panning action may be executed within the cropped area if fully contained within the cropped area. The system may further respond to the panning action coming within a predefined distance from a boarder of the current cropped area by replacing the current cropped area with a new cropped area of similar size as the current cropped area and shifted from the currently cropped area.

To facilitate the management of patient data across multiple ophthalmic systems on a computer network, the system may, in response to gaining access to the computer network, announce its presence to other computing systems on the computer network. The system may automatically identifying at least one other computing system on the network that has needed patient records and retrieve, over the computing network, the needed patient records from the at least one other computing system excluding any images associated with the retrieved needed patient records. The images may be retrieved later, if needed. For example, in response to user selection of a target option associated with a retrieved patient record, the system may initiate retrieval of the images associated with the target option irrespective of whether the user has elected to view any image associated with the target option.

Other objects and attainments together with a fuller understanding of the invention will become apparent and appreciated by referring to the following description and claims taken in conjunction with the accompanying drawings.

The embodiments disclosed herein are only examples, and the scope of this disclosure is not limited to them. Embodiments according to the invention are disclosed in the attached claims directed to a method, a storage medium, a system, a device and/or a computer program product, wherein any feature mentioned in one claim category, e.g. method, can be claimed in another claim category, e.g. system, as well. The dependencies or references back in the attached claims are chosen for formal reasons only. However, any subject matter resulting from a deliberate reference back to any previous claims can be claimed as well, so that any combination of claims and the features thereof are disclosed and can be claimed regardless of the dependencies chosen in the attached claims.

BRIEF DESCRIPTION OF THE DRAWINGS

In the drawings wherein like reference symbols/characters refer to like parts:

FIG. 2 illustrates an example of an enclosure system for the optical system of FIG. 1.

FIG. 3*aa* illustrates an example of actuating a privacy icon.

FIG. 12 illustrates the displaying of an image with zero zoom.

FIG. 13 illustrates a zoom operation in accord with some embodiments.

DESCRIPTION OF THE PREFERRED EMBODIMENTS

General System Considerations

Figure 1:
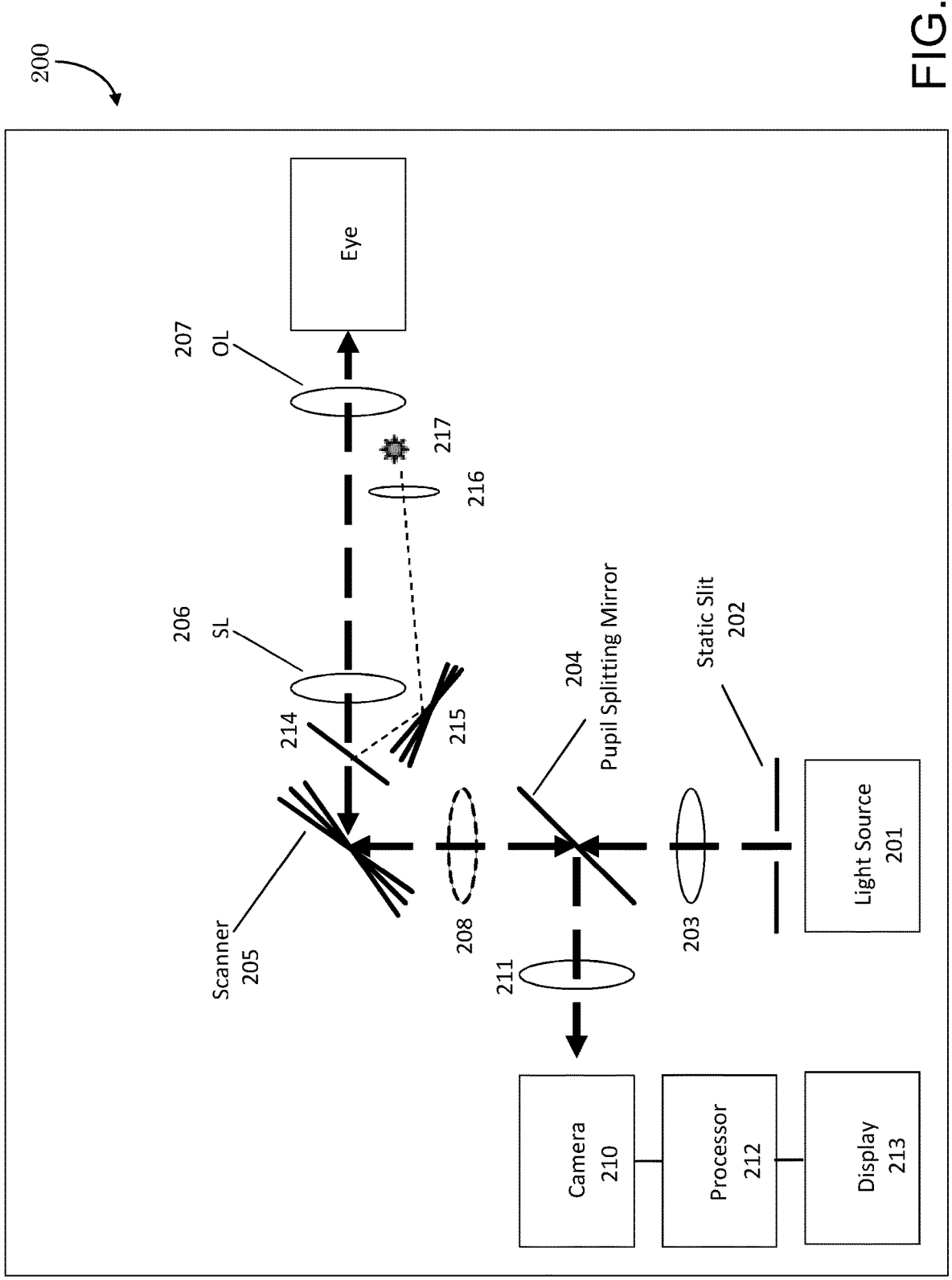
FIG. 1 illustrates an example of a slit scanning ophthalmic system.

FIG. 1 illustrates an example of a slit scanning ophthalmic system. As depicted, the system 200 includes one or more light sources 201, preferably a multi-color LED system or a laser system in which the etendue has been suitably adjusted. An adjustable slit 202 is positioned in front of the light source 201 to determine the illumination line width. This could also be established by the source independent of a slit or aperture. In the embodiment shown on FIG. 1, the slit 202 remains static during the imaging but can be adjusted to different widths to allow for different confocality levels and different applications either for a particular scan or during the scan for use in suppressing reflexes. An objective lens 203 forms a pupil of the slit. The objective lens 203 can be any one of state of the art lenses including but not limited to refractive, diffractive, reflective, or hybrid lenses/systems. The light passes through a pupil splitting mirror 204 and is directed towards a scanner 205. It is desirable to bring the scanning plane and the pupil plane as near together as possible to reduce vignetting in the system. Optional optics 208 may be included to manipulate the optical distance between the images of the two components. The splitting mirror 204 may pass an illumination beam from light source 201 to scanner 205, and reflect a detection beam from scanner 205 (e.g., reflected light returning from eye 209) toward camera 210. A task of the pupil splitting mirror (e.g., pupil splitter) 204 is to split the illumination and detection beams and to aid in the suppression of system reflexes. The scanner 205 could be a rotating galvo scanner or other types of scanners (e.g., piezo or voice coil, micro-electromechanical system (MEMS) scanners, electro-optical deflectors, and/or rotating polygon scanners). Depending on whether the pupil splitting is done before or after the scanner 205, the scanning could be broken into two steps wherein one scanner is in the illumination path and a separate scanner is in the detection path. Specific pupil splitting arrangements are described in detail in US Patent Publication No. 2015/0131050, the contents of which are hereby incorporated by reference).

From the scanner 205, the light passes through one or more optics, in this case a scanning lens (SL) 206 and an ophthalmic or ocular lens (OL) 207, that allow for the pupil of the eye 209 to be imaged to an image pupil of the system. One possible configuration for these optics is a Kepler type telescope wherein the distance between the two lenses is selected to create an approximately telecentric intermediate fundus image (4-f configuration). The ophthalmic lens 207 could be a single lens, an achromatic lens, or an arrangement of different lenses. All lenses could be refractive, diffractive, reflective or hybrid as known to one skilled in the art. The focal length(s) of the ophthalmic lens 207, scan lens 206 and the size and/or form of the pupil splitting mirror 204 and scanner 205 could be different depending on the desired field of view (FOV), and so an arrangement in which multiple components can be switched in and out of the beam path, for example by using a flip in optic, a motorized wheel, or a detachable optical element, depending on the field of view can be envisioned. Since the field of view change results in a different beam size on the pupil, the pupil splitting can also be changed in conjunction with the change to the FOV. For example, a 45°-60° field of view is typical for fundus cameras. Higher fields of view (60°-120°) may be desired for a combination of the Broad-Line Fundus Imager (BLFI) with other imaging modalities such as optical coherence tomography (OCT). The upper limit for the field of view will be determined by the accessible working distance in combination with the physiological conditions around the human eye. Because a typical human retina has a FOV of 140° horizontal and 80°-100° vertical, it may be desirable to have an asymmetrical field of view for the highest possible FOV on the system.

The light passes through the pupil of the eye 209 and is directed towards the retinal or fundus surface. The scanner 205 adjusts the location of the light on the retina or fundus such that a range of transverse locations on the eye are illuminated. Reflected or scattered light (or emitted light in the case of fluorescence imaging) is directed back along the same path as the illumination. At the pupil splitting mirror 204, the reflected light is separated from the illumination light and directed towards a camera 210. An objective lens 211 exists in the detection path to image the fundus to the camera 210. As is the case for objective lens 203, objective lens 211 could be any type of refractive, diffractive, reflective or hybrid lens as is known by one skilled in the art. Additional details of the scanning, in particular, ways to reduce artifacts in the image, are described in PCT Publication No. WO2016/124644, the contents of which are hereby incorporated by reference. The camera captures the received image, e.g., it creates an image file, which can be further processed by one or more processors.

Herein, the camera 210 is connected to a processor 212 and a display 213. These processing and displaying modules can be part of the system 200 itself, or may be part of a separate, dedicated processing and displaying unit, such as a computer system wherein data is passed from the camera 210 to the computer system over a cable or network including wireless networks. The display and processor can be an all in one unit. The display can be a traditional display or of the touch screen type and can include a user interface for displaying information to and receiving information from an instrument operator or user. The user can interact with the display using any type of user input as known to those skilled in the art including, but not limited to, mouse, knobs, buttons, and touch screen. The optical system illustrated in FIG. 1 is typically contained in an (e.g., plastic) enclosure for protection and includes components to interface with the patient.

FIG. 2 illustrates an example of an enclosure 250 for the optical system of FIG. 1. Enclosure 250 (e.g., the instrument) is be positioned on a surface 258 (e.g. an adjustable table) and is coupled to a patient interface 259, which includes a headrest 251 and/or a chinrest 252 for supporting the patient (or subject) 257. Various portions of the instrument and/or patient interface can be moved relative to each other to facilitate alignment of the instrument with the subject 257 being imaged, for example, using hardware controls such as joystick 253, and knobs 254 and 255. The display (not shown in this figure) can also be mounted on the table. Ophthalmic lens 207 provides the aperture for image acquisition.

It is desirable for the patient's gaze to remain fixed while imaging is carried out. One way to achieve this is to provide a fixation target that the patient can be directed to stare at. Fixation targets can be internal or external to the instrument depending on what area of the eye is to be imaged. One embodiment of an internal fixation target is shown in FIG. 1. In addition to the primary light source 201 used for imaging, a second optional light source 217, such as one or more LEDs, can be positioned such that a light pattern is imaged to the retina using lens 216. A scanning element (fixation scanner) 215 can be positioned such that it is located at the pupil plane of the system so that the pattern on the retina can be moved depending on the desired fixation location. Fixation locations can be preset in the system or customized by the user. In one embodiment, a system can have a fixed number of preset locations. When a preview image is displayed to the user (e.g., doctor or technician), the user can indicate where on the image, fixation is desired using a mouse or touch screen or other input device, and the system will select the closest preset fixation location and adjust the fixation scanner 215 accordingly. In addition, if a custom fixation location is desired, the user may indicate this in a different manner. For example, a user may indicate a desired custom fixation location by a double click or a long click of a button (physical or icon image). In this case, the system will adjust the fixation target to the user specified location. In most ophthalmic systems, the fixation target is turned off while it is being adjusted, but it may be beneficial to leave it illuminated as it is repositioned, such as to draw the subject's attention to the fixation target. In addition, it is possible to have the fixation target blink for a fixed amount of time in order to draw the subject's attention to it. Adjusting fixation is particularly important for montaging multiple images, which will be discussed in further detail below in the section entitled "Montaging Considerations".

In the configuration shown in FIG. 1, scattered light returning from the eye 209 (e.g., a collection beam) is "descanned" by scanner 205 on its way to pupil splitting mirror 204. That is, scanner 205 scans the illumination beam from pupil splitting mirror 204 to define a scanning illumination beam across eye 209, but since it also receives returning light from eye 209 at the same scanning position, scanner 205 has the effect of descanning the returning light (e.g., cancelling the scanning action) to define a non-scanning (e.g., steady or stationary) collection beam sent to pupil splitting mirror 204, which in turn folds the collection beam toward 210. Thus, the collection beam (from all scan positions of the scanning illumination beam) is applied to the same sensor region of the camera 210. A full-frame image may be built up (e.g., in processor 212) from a composite of the individually captured collection beams (resulting from the scanning illumination beam), such as by montaging. However, other scanning configuration are also contemplated, including ones where the illumination beam is scanned across the eye 209 and the collection beam is scanned across a photosensor array of the camera. PCT Publication WO 2012/059236 and US Patent Publication No. 2015/0131050, hereby incorporated by reference, describe several embodiments of slit scanning ophthalmoscopes including various designs where the returning light is swept across the camera and where the returning light is not swept across the camera. While the detailed description is focused on slit scanning ophthalmoscope, many of the system elements described herein, in particular the user interface elements, may be applied to other types of ophthalmic imaging and diagnostic systems.

Slit-scanning ophthalmoscope systems are capable of operating in different imaging modes depending on the light source and wavelength selective filtering elements employed. True color reflectance imaging (imaging similar to that observed by the clinician when examining the eye using a hand-held or slit lamp ophthalmoscope) can be achieved when imaging the eye with a sequence of colored LEDs (red, blue and green). Images of each color can be built up in steps with each LED turned on at each scanning position or each color image can be taken in its entirety separately. The three color images can be combined to display the true color image or they can be displayed individually to highlight different features of the retina. The red channel best highlights the choroid, the green channel highlights the retina, and the blue channel highlights the anterior retinal layers. Individual colored LEDs can be used to excite different fluorophores in the eye and the resulting fluorescence can be detected by filtering out the excitation wavelength. For example, fundus auto-fluorescence (FAF) imaging can be carried out with green or blue excitation which stimulates the natural fluorescence of lipofuscin, generating a monochrome image. The system can provide an infrared (IR) reflectance image, such as by using an infrared laser. The infrared (IR) mode is advantageous in that the eye is not sensitive to the IR wavelengths. This may permit a user to continuously take images without disturbing the eye (e.g., in a preview/alignment mode) to aid the user during alignment of the instrument. Also, the IR wavelengths have increased penetration through tissue and may provide improved visualization of choroidal structures. In addition, fluorescein angiography (FA) and indocyanine green angiography (ICG) imaging can be accomplished by collecting images after a fluorescent dye has been injected into the subject's bloodstream.

As the system relies on splitting the illumination and collection light at the pupil of the eye, the pupil should be large enough to allow for this condition. In addition, as described in International Application No. PCT/EP2018/058138, the contents of which are hereby incorporated in their entirety by reference, it can be beneficial to use multiple illumination paths. Adding multiple illumination paths through the pupil of the eye is facilitated by a larger pupil assuming that one keeps the initial illumination and collection apertures the same. A pupil can be enlarged (dilated) by adding mydriatic drops, but this is not always desirable as it has a short term impact on a person's vision. Imaging through pupils that have not been dilated with mydriatic drops is generally referred to as non-mydriatic or non-myd imaging, versus myd or mydriatic imaging in the case when the drops are used. As the pupil size varies among humans, the initial pupil size prior to dilation may not be sufficient for adding a second illumination path. Therefore it is desirable for the slit scan ophthalmic imager to have two modes, one for non-mydriatic imaging using a single illumination path to define a single illumination area on the pupil, and the other for mydriatic imaging, using multiple illumination paths defining multiple illumination areas on the pupil.

User Interface Elements

Slit-scanning ophthalmoscope systems, and ophthalmic imaging and diagnostic systems in general, can have a number of user interface screens with different viewports (e.g., framed areas on a display screen for viewing information), display elements and icons to guide an instrument operator through the steps involved with imaging including, but not limited to, entering patient information, setting acquisition parameters, reviewing, and analyzing data.

Figure 3A:
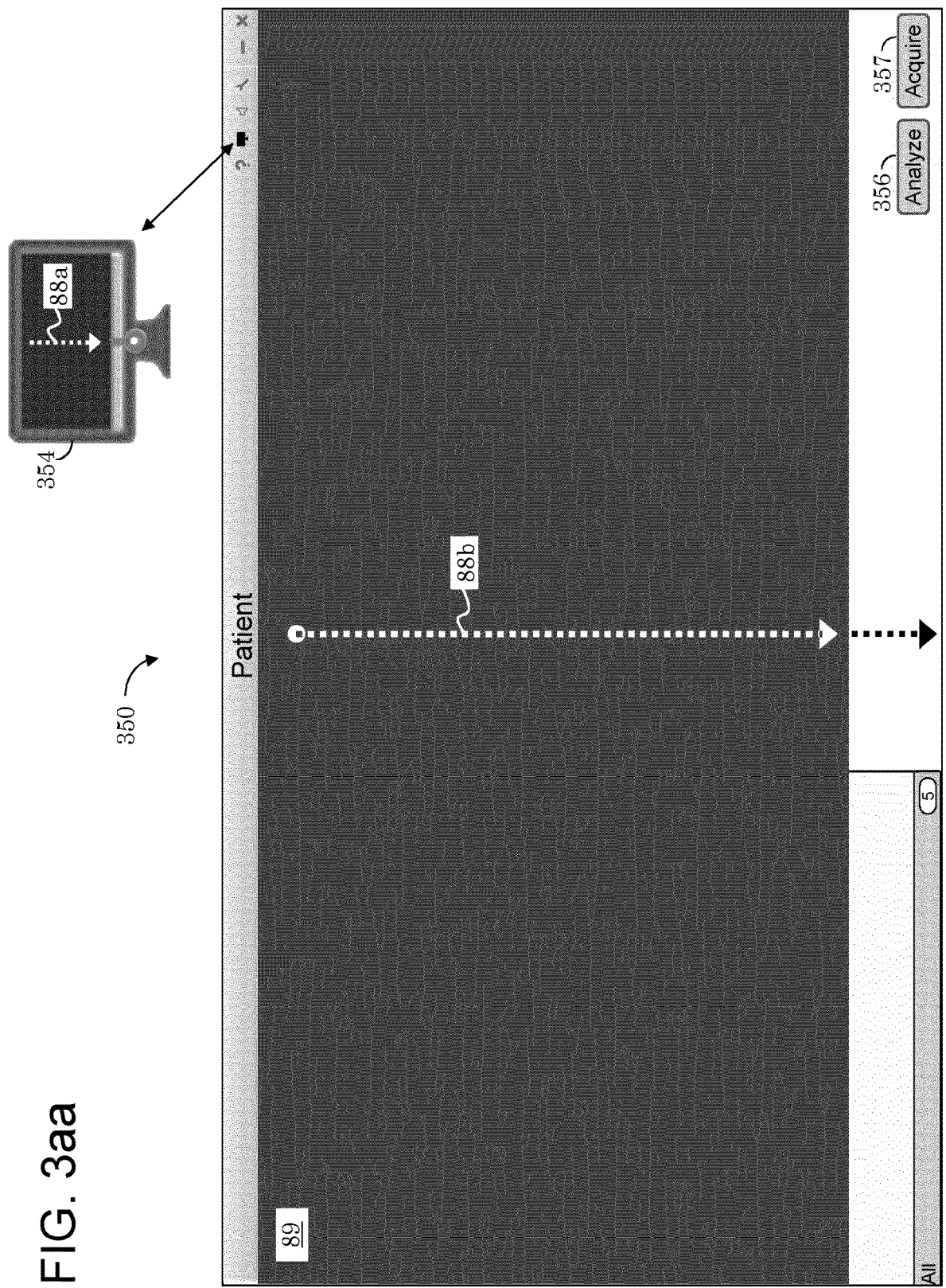
FIG. 3*a* shows an example of a patient information screen, e.g., user interface window focused on patient information, and providing a portal where a user may search for, edit, and/or add patient records.

FIG. 3a shows an example of a patient information screen 350, e.g., user interface window focused on patient information, and providing a portal where a user may search for, edit, and/or add patient records. The term screen, as used herein, may include an information display region rendered on a computer display, or may refer to the computer display itself, as can be understood from context. The information display region, along with any other display regions, icons, buttons, scrollbars, slide bars, menus, search windows, etc. described herein may be part of a graphical user interface, GUI. Although some embodiments of the present invention are portrayed as being a part of an ophthalmic device (or system), GUI elements described herein may be displayed on screens separate from the ophthalmic device. The present GUIs, and at least some of the ophthalmic information they provide, may be displayed on a screen of a computing device remote from an ophthalmic device. This computing device may be, for example, a desktop computer, a notebook computer, tablet computer or other portable computing device such as a smart phone, all of which may be retrieve information for display in the GUI from the ophthalmic device or from a local or remote data store of ophthalmic information, such as through a local or wide-area computer network (e.g., the Internet).

Figure 3B:
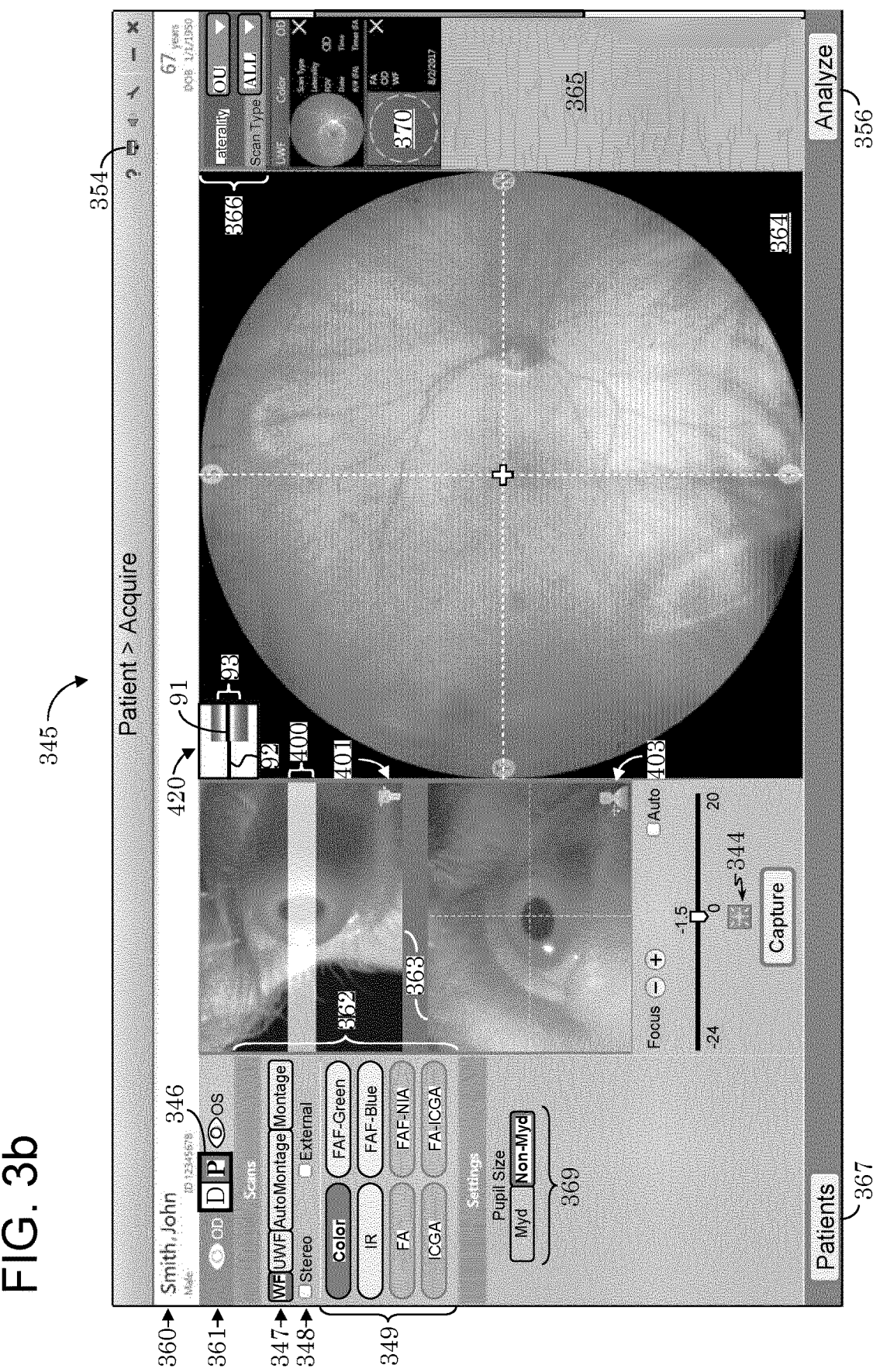
FIG. 3*b* shows an example of an acquisition window/screen used for acquiring (e.g., capturing) patient images.
Figure 3C:
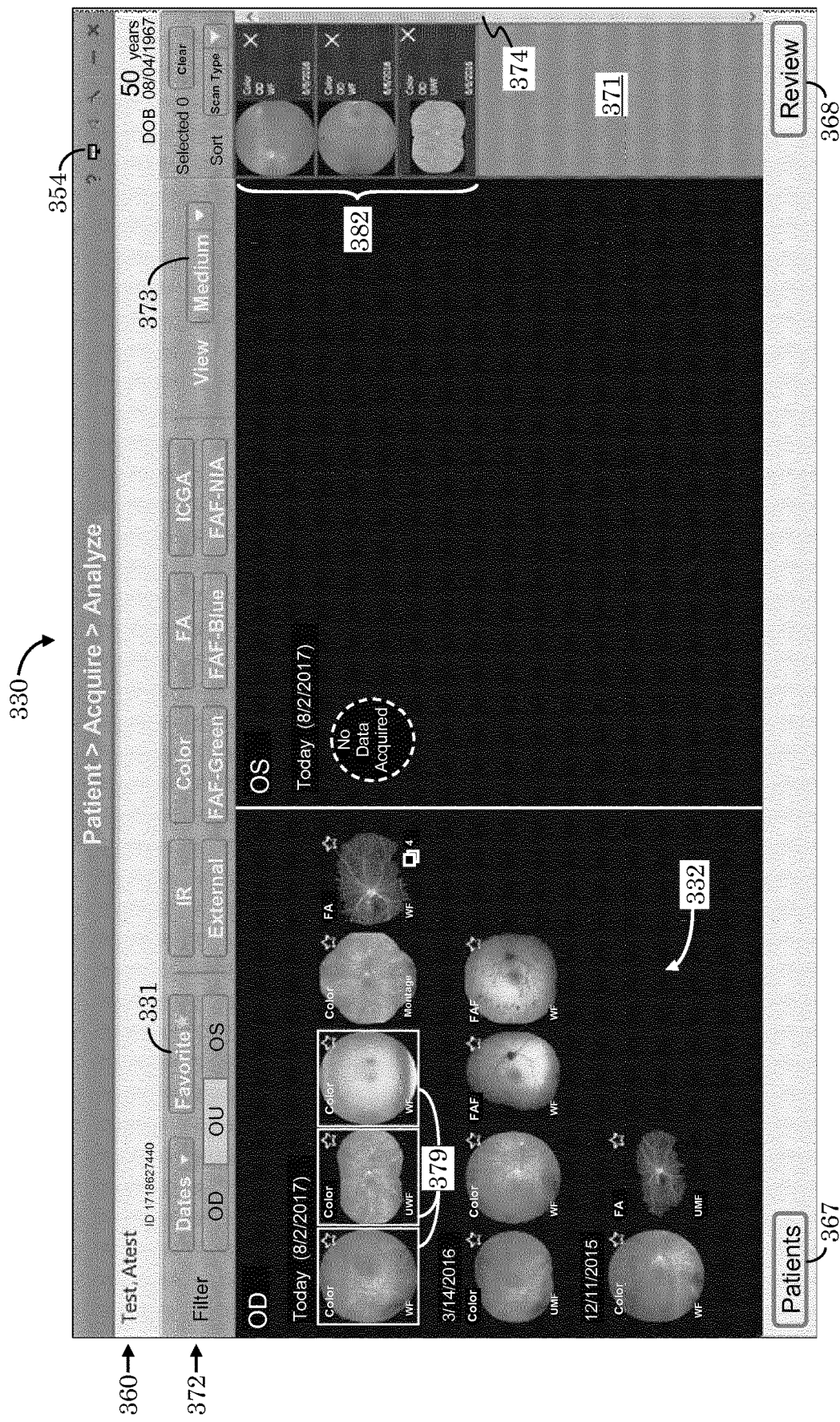
FIG. 3*c* shows an exemplary user interface for displaying the collected images, and for allowing the user to select images for further analysis, also referred to herein as a Proofsheet display/screen.

A search window 351 can be provided in which search criteria may be entered. For example, the user may type in a patient name, a patient identification number, a date of birth, or other patient identifier (e.g., last day of clinic visit). A processor (computer system) searches a database of existing patient records to see if a matching patient record already exists in the database. A list of possible patients 341 meeting the search criteria could appear in list form below the search window 351. The list of patients 341 could be further filtered using one of multiple, labeled filter option buttons, such as "Today", "Date", "Age Range", "Gender", etc., any of which may trigger a drop down menu of options. For example, a display element (button) labeled "Today" 353 may, when actuated/selected by the user using a user input device such as a mouse or finger touch, limit the search results to patients with appointments scheduled for today. Alternatively, the list may be filtered for patients on any given date specified by selecting the "Date" filter (not shown). Further alternatively, selecting the "Age Range" filter (not shown), may provide a drop down menu of age range options, such as "child", "teen", "20s", "30s", etc., and the list of patients may be filtered by a selected Age Range option. Patient data could also be pulled from another (e.g., remote) database such as an electronic medical record (EMR) database over a networked connection (e.g., the Internet). An advanced search button 310 could be provided which would open another window on the display with more detailed search fields. When a specific user is highlighted, as illustrated by a darkened or altered coloration area 355, the specific data for that patient is displayed in another portion of the screen, in this case on the right hand side of the patient information screen 350. The specific data may include a history section 342. In the history section 342, all scans or diagnostic data that have been previously collected on the patient can be displayed. Selectable buttons are provided on the patient information screen 350 to enter the other user interface displays, in this case "Analyze" (356) and "Acquire" (357). For example, selecting Acquire button 357 may transition to an acquisition screen 345, as shown in FIG. 3*b*, and selecting Analyze button 356 may transition to a Proofsheet display 330, as shown in FIG. 3*c*. Given the sensitivity of health records and the need for operators to leave patients in the room with instruments without supervision, it is desirable to have a way to quickly hide the data without following a standard log-out/log-in sequence. In the user interface shown in FIG. 3*a*, an icon, in this particular case, an image of a window shade (privacy icon 354) is displayed on the title bar of the patient information screen 350.

FIG. 3*aa* illustrates an example of actuating the privacy icon 354 of FIG. 3*a*. At any time, if the user selects the privacy icon 354 through a user input device (e.g., mouse or touch screen), the patient information screen 350 can be immediately changed to a privacy screen in which no patient data is displayed or a select portion of patient data is hidden or otherwise removed from display. Optionally, privacy icon 354 may respond to being selected by instantly portraying a darkened screen or illustrating a downward motion of its window shade as illustrated by dotted line 88*a*, e.g., in a manner similar to pulling down a window shade over a house window. The privacy screen on patient information screen 350 could be completely blank or display a logo or instructions as to how to remove the privacy screen and re-enter the system. The privacy screen could appear immediately or be designed to appear as an overlay 89 that rolls or slides, as illustrated by dotted arrow 88*b*. Optionally, the downward motion 88*b* of overlay 89 may mimic the downward motion 88*a* of the window shade on privacy icon 354. In one embodiment, a user may indicate a desire to exit the privacy screen by selecting (e.g., by mouse clicking or screen touching) any area on the privacy screen. Optionally, the system could respond by prompting the user for a valid password before removing the privacy screen, or could respond by immediately removing the privacy screen without requiring any password or other user-identification operation. While this privacy screen is described in the context of the patient information user interface (e.g., patient information screen 350), it could be displayed on any of the system's user interface screens. It is desirable to keep window shade (or privacy) icon 354 in the same location (e.g., the same location on the title bar) on all the system's user interface screens for easy access.

FIG. 3*b* shows an example of an acquisition window/screen 345 used for acquiring (e.g., capturing) patient images. In this window, various display elements and icons are displayed to the instrument operator (the user) to select the types of images to be acquired and to ensure the patient is properly aligned to the instrument. Patient data 360 of the currently selected patient can be displayed on the top of the acquisition screen 345. The laterality is displayed, e.g., via laterality icon(s) 361, highlighting which eye is being imaged (e.g., the right eye (oculus dexter) OD or the left eye (oculus sinister) OS). The graphical layout of laterality can be displayed from the doctor's point of view or from the patient's point of view. A single click of a mouse or finger touch on the laterality area 361 can toggle the laterality designation from the patient's point of view to the doctor's point of view, and vice versa. Optionally, the laterality icon 361 may include a point-of-view indicator 346 indicating whether the laterality point of view currently being displayed is the doctor's ("D") or the patient's ("P").

Different scan options are displayed on one section of the acquisition screen 345, in this case section/area 362. The scan options may include FOV buttons 347 for the user to select an imaging FOV (e.g., wide-field (WF)—standard single image operation, ultra-wide-field (UWF)—montage of two images, AutoMontage—a preset montage sequence collecting four images, or Montage—a user specified montage sequence) of one or more images to be acquired. The scan options may also include scan type buttons 349 for selecting between, for example, options Color (e.g., true color imaging including red, green, and blue light components), IR (imaging using infrared light, e.g., a IR laser), FAF-Green (fundus auto-fluorescence with green excitation), and FAF-Blue (fundus auto-fluorescence with blue excitation). In addition, checkboxes 348 can be provided to indicate whether a user wishes to perform stereo imaging and/or use an external fixation target. Selecting the external fixation target, will disable the internal fixation target in the system during imaging.

The acquisition screen 345 displays one or more pupil streams 363 of live images of the pupil of the eye to aid in alignment, as will be described in further detail in the section entitled "Alignment Considerations". Pupil streams 363 may provide controller icons (or controller animations/illustrations) 401 and 403, which may correspond to joystick 253 of FIG. 2 and convey manipulation information/instructions for joystick 253 to aid the user in achieving proper alignment.

The user can select between mydriatic (Myd) and non-mydriatic (Non-Myd) imaging modes by selecting the button for the respective mode 369. As will be described in further detail below, it is also possible for the system to automatically choose (e.g., auto-select) which mode is appropriate based on conditions of the eye.

A stream of live preview images 363 can be displayed in a section of the acquisition screen 345 to indicate the current imaging conditions. Preview images 363 are continuously updated as alignment adjustments are made to provide the instrument user with an indication of the current image quality.

A blink icon 344 to cause the fixation target to blink (e.g., strobe on and off) can be provided. Selection of blink icon 344 can cause the system to blink the fixation target for a preset amount of time, or until the user activates the blink icon 344 again. This can help draw the attention of the patient to the fixation target.

As images are captured, they can be displayed in thumbnail form in a section of the acquisition screen 345, in this case section/area 365, termed the Capture Bin. Display elements such as drop down list 366 can be used to refine the thumbnails displayed in the Capture Bin 365 (e.g., laterality, imaging mode, etc.). Similar to the patient information screen 350 of FIG. 3a, selectable display elements can be provided to transition to the other user interface screens, in this case, buttons "Patients" 367 and "Analyze" 356 can be used to transition to other screens. For example, selection of "Patients" button 367 may transition to the patient information screen 350 of FIG. 3a, and selection of "Analyze" button 356 may transition to a Proofsheet display 330 of FIG. 3c. Note that the Privacy screen icon 354 is placed in the same location on the title bar of the acquisition screen 345 as on the patient interface screen 350 for easy access. In addition, if an imaging mode is selected that requires the acquisition of multiple images (e.g., UWF, AutoMontage), the Capture Bin 365 can be pre-populated with placeholder icons 370 (e.g. dashed circle) indicating placeholders for the images to be captured, and the placeholder icons 370 can be replaced with thumbnails of the captured images as they are acquired to provide the user with an indication of the status of the imaging.

FIG. 3c shows an exemplary user interface for displaying the collected images, and for allowing the user to select images for further analysis, referred to herein as the Proofsheet display/screen 330. Similar to the acquisition screen 345, patient data 360 can be provided to the user, in this embodiment, at the top of the screen 330. The collected images for a particular patient can be grouped and displayed as a list of thumbnails 332 in one or more viewports on the screen 330 in a number of ways as would be recognized by someone skilled in the art. In the embodiment displayed in FIG. 3c, the primary image grouping is by laterality (OD/OS). The images can be further grouped by date acquired. Since a large quantity of data could exist, the ability to scroll down through the images is provided by mouse or finger touch of a scroll bar 374. Display elements 372 such as drop down lists or selection buttons are provided for the user to further filter the images displayed at any time. One set of filter options could be user configurable (331), in which the user preselects their most popular or favorite types of images, and this drop down list is provided on the Proofsheet screen for them to select from. In this particular embodiment, the user can select images (for example, from among thumbnails 332) for further analysis by a single click, which will result in a thumbnail of the selected image(s) 382 being placed in the Selection Bin 371 on the right hand side of the screen 330 and the selected image(s) 379 in thumbnail list 332 being highlighted in some manner (e.g., a colored frame or bright frame outline), to make it clear to the user that this particular image has been selected from thumbnails list 332 for further analysis. Other means of selection such as drag and drop can also be envisioned by someone skilled in the art. The size of the thumbnails 332 can be adjusted (such as to display a larger number of thumbnails) by a drop down menu 373 or other user input element such as a slider bar. Similar to the patient information screen 350 of FIG. 3a and the acquisition screen 345 of FIG. 3b, selectable display elements can be provided to transition to the other user interface screens, in this case, "Patients" 367 and "Review" 368. For example, selection of "Patients" buttons 367 may transition to the patient information screen 350 of FIG. 3a, and selection of "Review" button 368 may transition to a review screen, such as shown of FIG. 3d. Note the Privacy screen icon 354 is placed in the same location as on the other user interface screens for easy and consistent access.

Figure 3D:
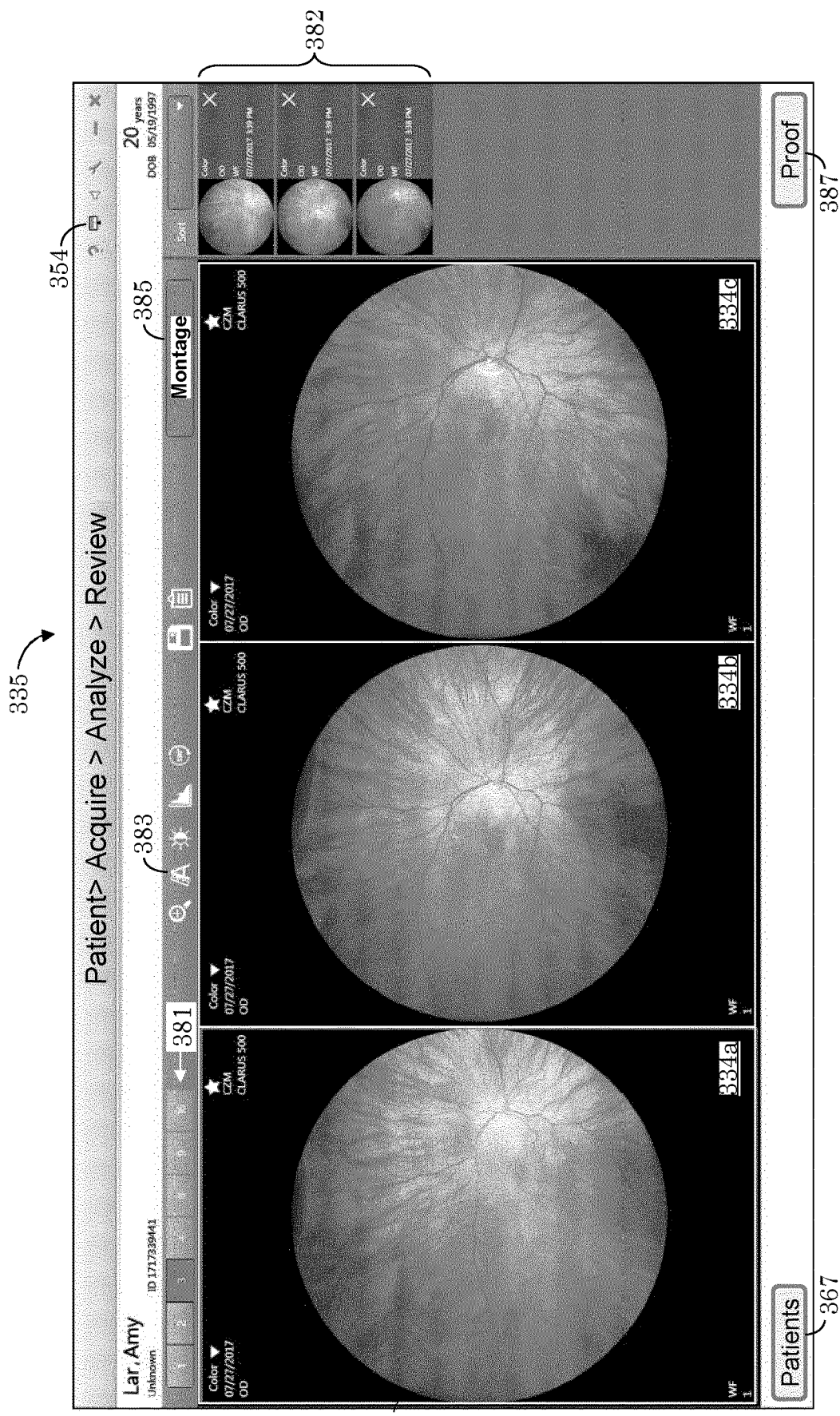
FIG. 3*d* illustrates one embodiment of a review screen, which can display for analysis the selected image data from the Proofsheet screen of FIG. 3*c*.

FIG. 3d illustrates one embodiment of a review screen 335 which can display for analysis the selected image data from the Proofsheet screen 330. A number of viewports (e.g., 334a, 334b, and 334c) can be displayed to the user with each viewport showing one image for further analysis. The exact number of viewports can be selected by the user, e.g., by selection of an appropriate number button 381 or a drop down list (not shown). The number of viewports can be restricted depending on filtering or imaging mode selections (e.g., if stereo imaging mode is selected, only even numbered of viewports are available and an icon indicating stereo mode (not shown) could be overlaid on the (or on select) number buttons 381). In one portion of the screen, it is possible to display the thumbnails 382 that were selected on the Proofsheet display 330 to allow the user to select which images are displayed in the viewports. A montage selection button 385 can be provided to montage together two or more selected images. An icon 383 (e.g., an icon of a letter with one side of the letter being a side of a ruler, or other measuring stick) can be displayed to the user to allow the user to make annotations and/or measurements on the image(s). It would be desirable for measurements or annotations that are made on one image to be propagated to other similar images (e.g., images including at least a part of substantially the same area of the retina from the same, or other designated, patient). Cases where this might be useful might include copying the outline of geographic atrophy as identified on a True Color image to an FAF-Blue image of the same area of the eye to see how the lesion extent differs between modalities. Another case might be copying annotations of one image from a prior visit to another image from a current visit (or vice versa) as a workflow aid and as a comparison to look for changes. Similar to the patient information screen 350 of FIG. 3a, the acquisition screen 345 of FIG. 3b, the Proofsheet screen 330 of FIG. 3c, selectable display elements can be provided to transition to the other user interface screens, in this case, "Patients" 367 and "Proof" 387. For example, selection of "Patients" buttons 367 may transition to the patient information screen 350 of FIG. 3a, and selection of "Proof" button 387 may transition to Proofsheet screen 330 of FIG. 3c. Note the Privacy screen icon 354 is placed in the same location as on the other user interface screens for easy and consistent access.

Figure 3E:
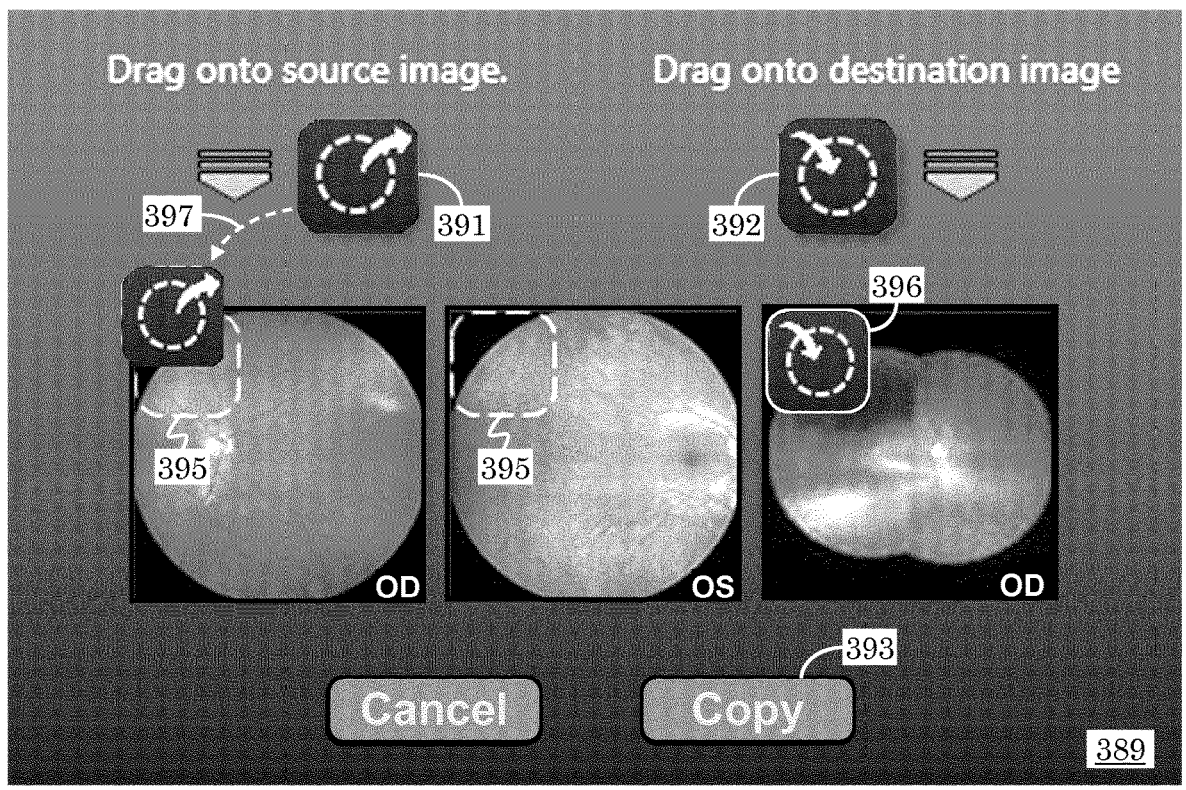
FIG. 3*e* illustrates an embodiment to facilitate the copying of annotations (and/or measurements) between images.

FIG. 3e illustrates an embodiment to facilitate the copying of annotations (and/or measurements) from one image to another. Here, a series of images (e.g., three images) are displayed in a copy panel 389. A source icon 391 (e.g., a "from" icon) and destination icon 392 (e.g., a "to" icon) indicate which images the annotations should be copied from and to, respectively. The source icon 391 depicts an eye or fundus image (e.g., a circle) with a first arrow exiting from it. The destination icon 391 depicts an eye or fundus image (e.g., a circle) with a second arrow entering it. Each image in the copy panel 389 contains a placeholder (region 395), and optionally also a laterality indicator (OD or OS)

specifying if the image is of a right eye or left eye. When either of the "from" or "to" icons is dragged onto an image, its placeholder 395 is populated with the corresponding icon. For example, dotted arrow 397 shows "from" icon 391 being dragged into the left-most image in copy panel 389. This will result in the source icon 391 populating the placeholder 395 of this left-most image. This shows the user whether that image has been designated as a "from" image, a "to" image, or neither. For example, the placeholder of the right-most image in copy panel 389 is shown populated with an image/icon 396 matching destination icon 392, indicating that annotations/measurements will be copied to this image.

Optionally, the user-made annotations (or measurements) on the source image file define an area/region of the source image file, and a matching area/region may be identified in the destination image file. The matching area in the destination image file may be identified, for example, by image registration of the source and destination image files, identifying corresponding structures (e.g., the fovea, optic disc, dominant vessel structures, etc.) in both source and destination image files, and/or direct mapping from a predefined corner (or other marker) of the source and destination image files. Irrespective of how the matching area/region is identified in the destination image file, optionally, the user-made annotations in the source image file may be copied to the matching area/region in the destination image file. In this manner, if annotations are made, for example, at a region located to the upper left of a definite structure, the annotations will be copied to a similar region to the upper left of a similar structure in the destination image file(s).

Figure 3F:
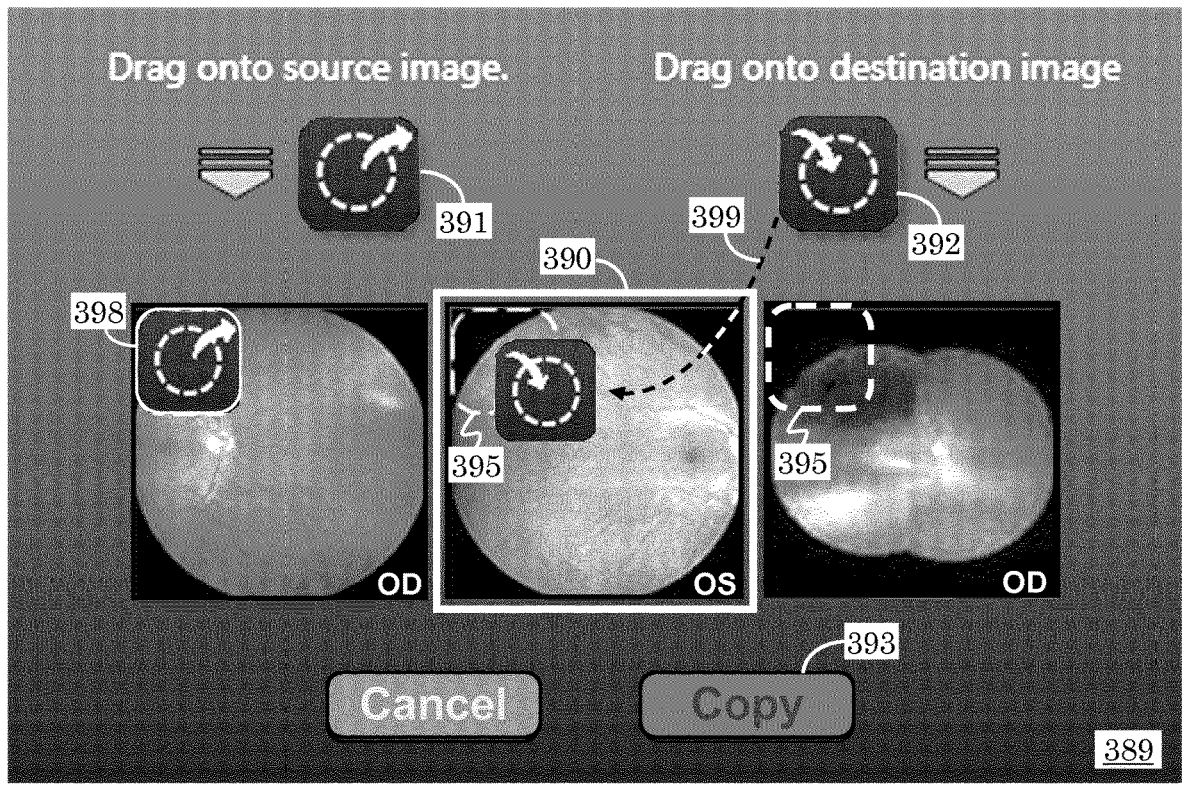
FIG. 3*f* illustrates an example depicting an error in the designation of a "source" image and a "destination" image.

FIG. 3f illustrates an example depicting an error in designating a "from" image and a "to" image. All elements similar to those of FIG. 3e have similar reference characters and are described above. When either source icon 391 or destination icon 392 is dragged to a second image (after having already been dragged to a first image), the second image will display the dragged icon, while the first image will revert to displaying the undesignated "placeholder" 395, ensuring that only one image at a time can be designated the "from" or "to" image for the purpose of copying annotations. Alternatively, multiple destination, or "to", images may be designated, in which case the annotation(s) of the "from" image will be copied to all designated "to" images. However in the present embodiment of FIG. 3f, which permits a single "from" image and a single corresponding "to" image, dotted arrow 399 shows the "to" icon 392 being dragged to the middle image after having already been dragged to the right-most image in FIG. 3e. Consequently, in the right-most image, icon 396 (from FIG. 3e) is replaced with placeholder 395. Normally, the middle image would then populate its placeholder 395 with an image of icon 392, but the middle image does not match the laterality of the currently designated "from" image (e.g., the left-most image). That is, the left-most image has a laterality of OD (e.g., right eye), while the middle image has a laterality of OS (e.g., left eye). Consequently, the middle image is highlighted as an error (e.g., by use of a highlighting frame 390), and copy button 393 is deactivated. That is, before copying the annotations, the user can be prompted once again by a confirmation button (e.g., the "copy" button) 393, which is made available only when a proper "to" image and a proper "from" image have been designated, to confirm the correct images and annotations have been selected. Because the images may have different fixation locations, it is desirable for the annotations and/or measurements to be corrected for distortions using an eye model that accounts for the differences in fixation as will be described in further detail below in the section entitled "Distortion Corrections".

It is typically desirable to compare the same type of images over time to look for changes. In order to facilitate this, it is possible to provide an easy or quick compare option whereby when a single image is selected by the user in some manner, the processor searches the available data for all images with the same imaging conditions as that image and quickly displays the collection of similar images. In a preferred embodiment, this action can be accomplished by right clicking on a particular image and selecting this functionality from a list of options. Upon selection, images of the same patient matching the imaging mode (Color, IR, FAF-Green, FAF-Blue, etc.), the laterality (OD/OS), the FOV (WF, UWF, Montage, etc.), and/or matching the fixation location (or direction/angle) are automatically identified by the processor and displayed in the review screen 335. Annotations may then be copied from a source image to multiple destination images (e.g., selected by the user) as group. The system defaults to display the most recent image on the left hand side and the historical images in one or more viewports next to it. The system can be further designed to maintain the most current image in one viewport while advancing through the historical images in chronological order, by button press, scroll wheel, automated movie playback, or by some other user input as would be recognized by someone skilled in the art. This would allow the user to easily visualize (e.g., visually identify or recognize) any changes over time.

Alignment Considerations

Figure 4A:
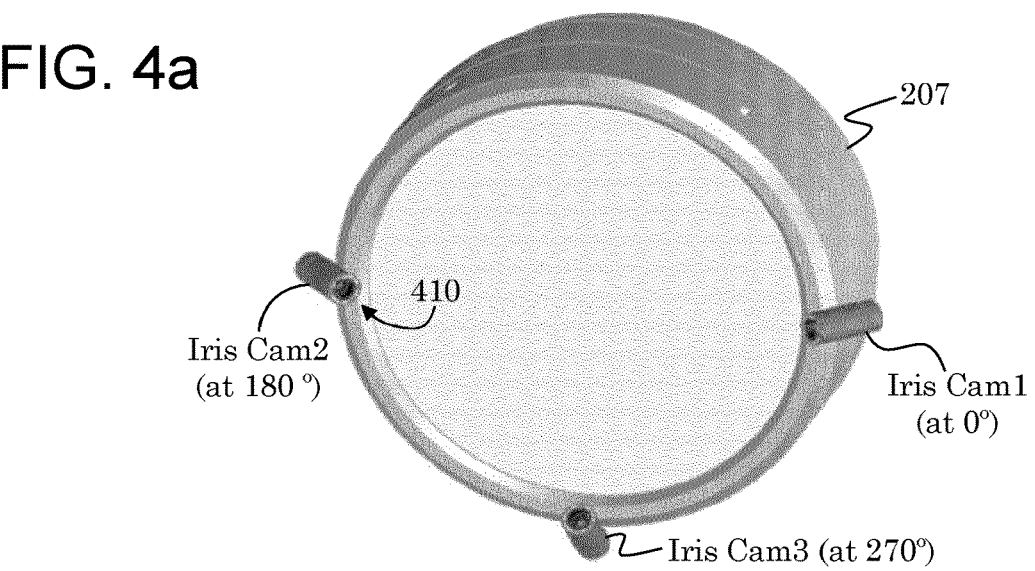
FIG. 4*a* illustrates the attachment of multiple iris cameras to an ophthalmic (or ocular) lens to facilitate alignment between an ophthalmic imaging instrument/device and a patient.
Figure 4B:
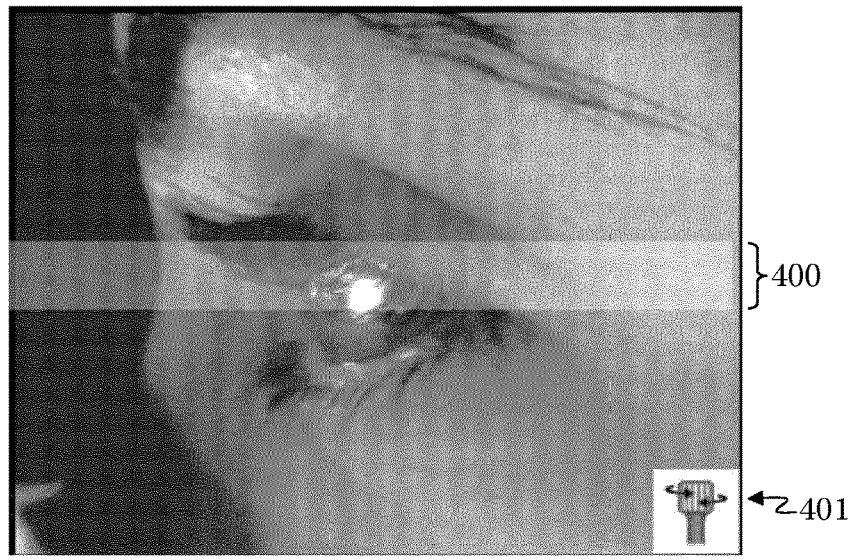
FIG. 4*b* shows an image collected from either the 0° or 180° iris cameras of FIG. 4*a*.
Figure 4C:
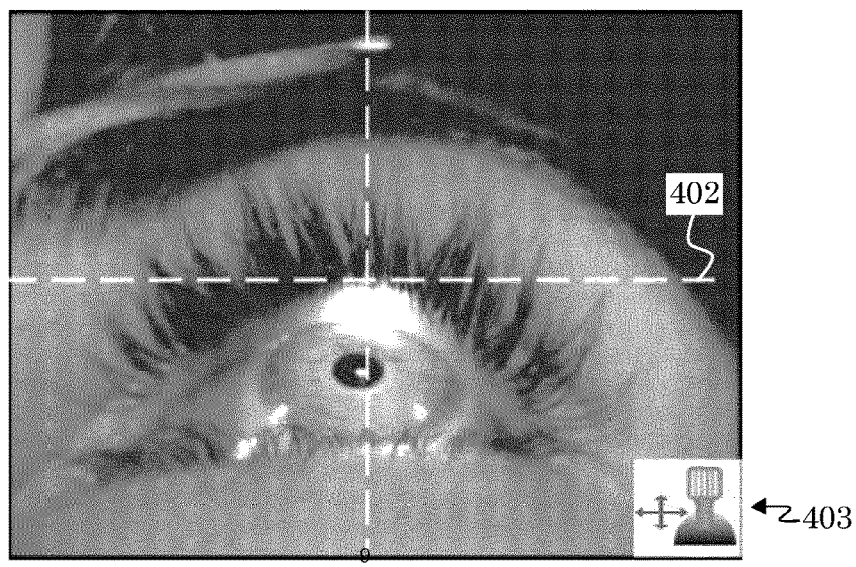
FIG. 4*c* shows an image collected from the iris camera of FIG. 4*a* located at 270°.

FIG. 4a illustrates the attachment of multiple iris cameras (e.g., Cam1, Cam2, and Cam3) to an ophthalmic (or ocular) lens 207 of an ophthalmic imaging system. The iris cameras are positioned to image the iris (e.g., positioned to image the exterior of the eye). This permits the collecting of images of the iris and pupil of the subject's eye, which may be used to facilitate alignment between an ophthalmic imaging instrument/device/system and a patient. In the embodiment illustrated in FIG. 4a, the iris cameras are installed roughly at 0, 180, and 270 degree positions around ophthalmic lens 207, from the patient's perspective, with respect to the ophthalmic lens 207. It is desirable for the iris cameras Cam1, Cam2, and Cam3 to work off-axis so that they do not interfere with the main optical path. The iris cameras provide live images of the patient's eye on the display (e.g., on the pupil streams 363 of acquisition screen 345 in FIG. 3b) to aid fine patient alignment and acquisition. FIG. 4b shows an image collected from either the 0° or 180° iris camera (e.g., Cam1 or Cam2) while FIG. 4c shows an image collected from iris camera Cam3 located at 270°. The iris camera images presented to the user can be a composite/synthetic image showing information about offset between the desired and the current location of the patient's pupil center. Operators can use this information to center the pupil and to set the correct working distance via the cross table with respect to the patient's eye. For example, FIG. 4b shows how an overlay guide (semi-transparent band 400) can be shown on the image to communicate the acceptable range in which the pupil can be positioned for good image acquisition. In addition, icon (or animation) 401 displays which (and how) hardware control or adjustment (on the ophthalmic device) should be made to the system to achieve the desired alignment (for proper alignment), in this case, a twist of the joystick 253 of FIG. 2. Similarly in FIG. 4c, dashed crosshairs 402 are displayed to indicate the desired location of the pupil for optimum imaging, and icon (or animation) 403 indicates that the joystick 253 should be translated (e.g., moved forward, backward, left, right, or a combination of these) to achieve optimal positioning of the instrument relative to the patient.

At least two iris cameras are needed to cover all three degrees of freedom (x,y,z) at any given time. Offset information is extracted by detecting the patient's pupil and locating the center of the pupil and then comparing it to stored and calibrated reference values of pupil centers. For example, iris camera Cam3 (located at the 270° position) maps the x coordinate of the patient's pupil center to the column coordinate of the iris camera image (which is comprised of rows and columns of pixels), while the z-coordinate is mapped to the row coordinate of the camera image. As the patient or the instrument moves laterally (e.g., right to left or left to right), the image moves laterally (e.g., right to left), and as the instrument is moved closer or further away from the patient, the image of the pupil will move up or down. The y-coordinate of the patient's pupil is extracted by one or both of the iris cameras located at 0° and 180° (Cam1 and/or Cam2) as they map the y-coordinate to different rows of the image.

This camera geometry is beneficial in that it provides more intuitive and useful image combinations to enable faster and more accurate patient alignment. The proposed system can also be very helpful in establishing an automatic patient alignment system based upon pupil detection and using the detected coordinates in a feedback loop. The advantage comes from the fact that having more than two cameras where the lines joining the camera centers to the target do not intersect in one plane (non-coplanar line of sight), provides better coverage and better precision in pupil detection. It is also well known that having cameras where the lines of sight are non-coplanar provides an easier way to calibrate the iris camera system.

In addition, it is possible to use integrated illumination as part of iris cameras instead of having a separate illumination source. For example, each of iris cameras Cam1, Cam2, and Cam3 may have one or more LEDs 410 around their front aperture. Optionally, the integrated iris illumination light source(s) operate in the infrared wavelength region (e.g., >780 nm) that makes their light completely transparent/invisible to a human eye and thus does not distract the patient. Additionally, long pass filters may be used in front of the camera sensor to filter out the effect of any alignment light being used to acquire an intermediate image. Integrated illumination also provides small package size allowing the operator a better view of the patient's eye. It is also noted that, the iris camera systems being used have the ability to turn the integrated illumination off when the retina camera(s) used to image the retina is being exposed. This system thus avoids the back-illuminating of the retina by the iris illumination source 410.

An advantage of this iris camera architecture scheme is the flexibility of using any of the iris cameras Cam1, Cam2 or Cam3 to determine the minimum pupil size and letting the operator decide if the alignment is sufficiently accurate to produce an artifact free fundus image. As previously described, an instrument can be used in different configurations, e.g., mydriatic mode where the patient's pupil is dilated by means of drops or if the patient naturally has a large pupil, and non-mydriatic mode where the pupil is constricted or otherwise not large enough for use in the mydriatic mode. In the case of non-mydriatic operation (e.g., used when the pupil size is below a minimum size for mydriatic mode), the instrument may not use full-power retina (or fundus) illumination, both/all illumination beams in the case of multiple illumination beam paths, and may reduce or change the shape of the retina illumination beam to allow imaging without clipping of the retina illumination light when it traverses the pupil. Thus, determining the pupil size from the iris cameras can have a direct effect on selection of a mode of operation. Similarly, comparing the pupil size, whether manually by the operator, or by an automatic algorithm allows the operator to determine when the patient is sufficiently aligned. This will result in shorter alignment time for the operator.

Figure 5A:
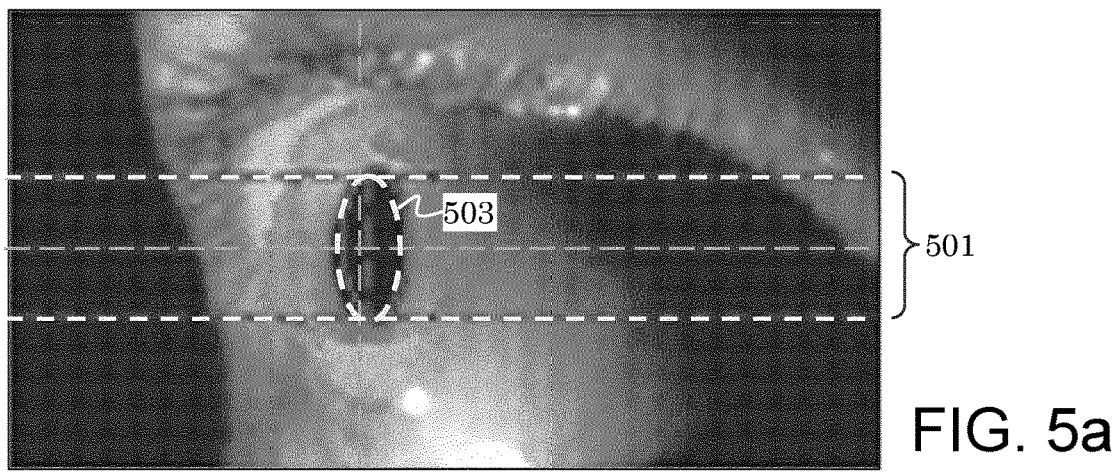
FIG. 5*a* illustrates the comparing (e.g., for alignment purposes) of a pupil imaged by one of the side cameras (e.g., located at 0° or 180°) of FIG. 4*a* to a reference minimum pupil size.
Figure 5B:
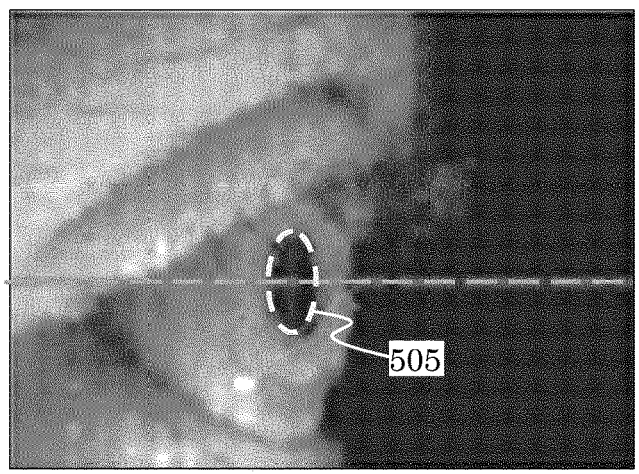
FIG. 5*b* displays an ellipse that shows a minimum pupil diameter requirement in both directions (e.g., in both the major axis and minor axis of the ellipse) and a reference center dash line that may be superimposed on an image obtained from the side cameras of FIG. 4*a*.
Figure 5C:
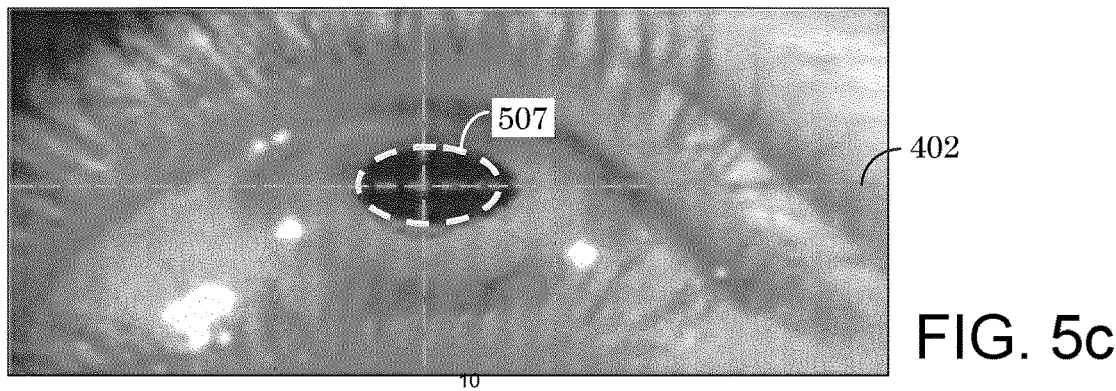
FIG. 5*c* illustrates an ellipse that shows the minimum pupil diameter requirement in both directions on an image obtained from the bottom iris camera of FIG. 4*a* (e.g., located at 270°).

FIGS. 5a to 5c show exemplary embodiments of how an imaged pupil may be compared to a reference minimum pupil size in one or more of the iris images. FIG. 5a illustrates the comparing (e.g., for alignment purposes) of a pupil imaged by one of the side cameras Cam1 or Cam2 (e.g., located at 0° or 180°) of FIG. 4a to a reference minimum pupil size. In FIG. 5a, two lines (or a bar) 501 indicate a minimum required pupil size for optimal imaging on an image obtained from the side cameras. As an indicator of proper alignment, the pupil should lie within lines 501. For ease of visualization, an outline (e.g., an ellipse) 503 of the pupil may be provided. FIG. 5b displays an ellipse 505 that shows a minimum pupil diameter requirement in both directions (e.g., in both the major axis and minor axis of the ellipse 505) and a reference center dash line that may be superimposed on an image obtained from the side cameras. For example purposes, FIG. 5b illustrates a proper pupil alignment as viewed from a side camera. FIG. 5c illustrates an ellipse 507 that shows the minimum pupil diameter requirement in both directions on an image obtained from the bottom iris camera of FIG. 4a (e.g., Cam3 located at 270°). Also shown are dashed crosshairs 402 used to indicate the desired location of the pupil for optimum imaging. For example purposes, FIG. 5c illustrates a proper pupil alignment as viewed from the bottom camera.

It is noted that the values of the major and minor axes of the pupil ellipse (503, 505, and 507) and/or the height of the bar or lines (501) are determined in a processor based upon pre-calibration, where a target instrument is used to determine the mapping between the minimum required pupil requirement due to the size and shape or the instrument and the image obtained from the iris cameras (Cam1, Cam2 and/or Cam3). It is also noted that a different set of such calibration values may exist to calibrate each iris camera individually and also to account for different imaging modes of the instrument, e.g., mydriatic versus non-mydriatic.

FIGS. 5a to 5c show embodiments where the overlay images are used by an operator to determine if the patient's pupil is aligned in such a way that it fulfills the minimum pupil diameter requirements of a particular mode of operation of an ophthalmic imaging system, in this case a slit scanning ophthalmoscope. As explained above, an operator may adjust the patient's alignment (e.g., using joystick 253 or manual control input) to bring the image of the patient's eye from the live feed into agreement with the overlay images. Additionally, automatic algorithms can also be used to extract the pupil diameter of the patient, and this extracted diameter can be compared with the known calibrated values of the minimum pupil diameter requirement of the instrument. In this case, a simple binary decision can be provided to the operator to start capturing. One can also put the instrument in an automatic mode where as soon as the extracted pupil diameter is larger than the minimum pupil size requirement of the instrument, and/or that the pupil location is confirmed for sufficient image quality, a fundus image is automatically taken. Additionally, the system could switch between non-mydriatic and mydriatic modes based on automated detection of the pupil size. If the pupil size requirement is achieved, the system can switch to mydriatic mode, and if the pupil is detected to be too small for mydriatic imaging, the system can automatically switch to non-mydriatic mode.

Brightness Adjustment

Human retinas can be lightly pigmented or darkly pigmented. If an image of equal flash intensity and exposure is taken on a darkly pigmented retina and on a lightly pigmented retina, the resulting output image could be too dark in the case of the darkly pigmented retina and saturated (e.g., overly bright) in the case of the lightly pigmented retina. These scenarios make it hard for an imaging device operator to adequately align the patient, which may result in a sub-optimal image capture. By having feedback on whether a lightly or darkly pigmented retina is being imaged, the flash (e.g., illumination on the retina camera) can be adjusted automatically to ensure a consistently bright image across differently pigmented retinas. In addition, during FA imaging, areas of hemorrhage, for example, could show up saturated. Similarly during ICG, areas of choroidal neovascularization could show up saturated. If a clinician were interested in looking into the details of these areas, such as in a live feed from the retina camera, this saturation would prevent them from seeing anything.

In consumer cameras, e.g., mobile phones, a similar problem exists and the problem is addressed by analyzing the images during preview and automatically adjusting the gain on the camera based on the brightness of a number of previous images. The issue with this approach for retinal imaging is that the retina camera is aligned to image in one specified direction (e.g., through the pupil to a target region of the fundus), and patient movement may cause the retina camera to image items that are not the retina. That is, it is only desirable to adjust the gain of the retina camera when imaging the patients' retina, and to not take into account eye blinks, which may show up as bright images due to an illumination beam reflecting off the eye lid, or eye movements that block light from getting into the eye, which may show up dark due to an illumination beam being clipped at the pupil as it enters the interior of the eye. In other words, the retina camera of the present system knows the target subject that is to be imaged (e.g., the fundus), and determines for each captured image whether the target subject is in the captured image (e.g., if the captured image is valid), and uses only captured images of the target subject for purposes of adjusting the camera gain. In terms of getting a consistently illuminated image, in the past, products have had a flash control that the operator could manually use to adjust the flash. The issue with this is that the operator is making the decision on what flash level to use, and this results in image brightness variability caused by operator variability. Here, a method for continuously imaging and analyzing an area, or region, of interest in the retina for purposes of adjusting the gain of the retina camera is described. The imaged area may be analyzed to determine if it is a valid imaging area, e.g., a retina as opposed to an eyelid, and if it is a valid imaging area, then the system makes a determination based on the image brightness whether to increase or decrease an Analog Gain on the retina camera. Optionally, the gain may be adjusted only when the image is in focus.

Figure 6:
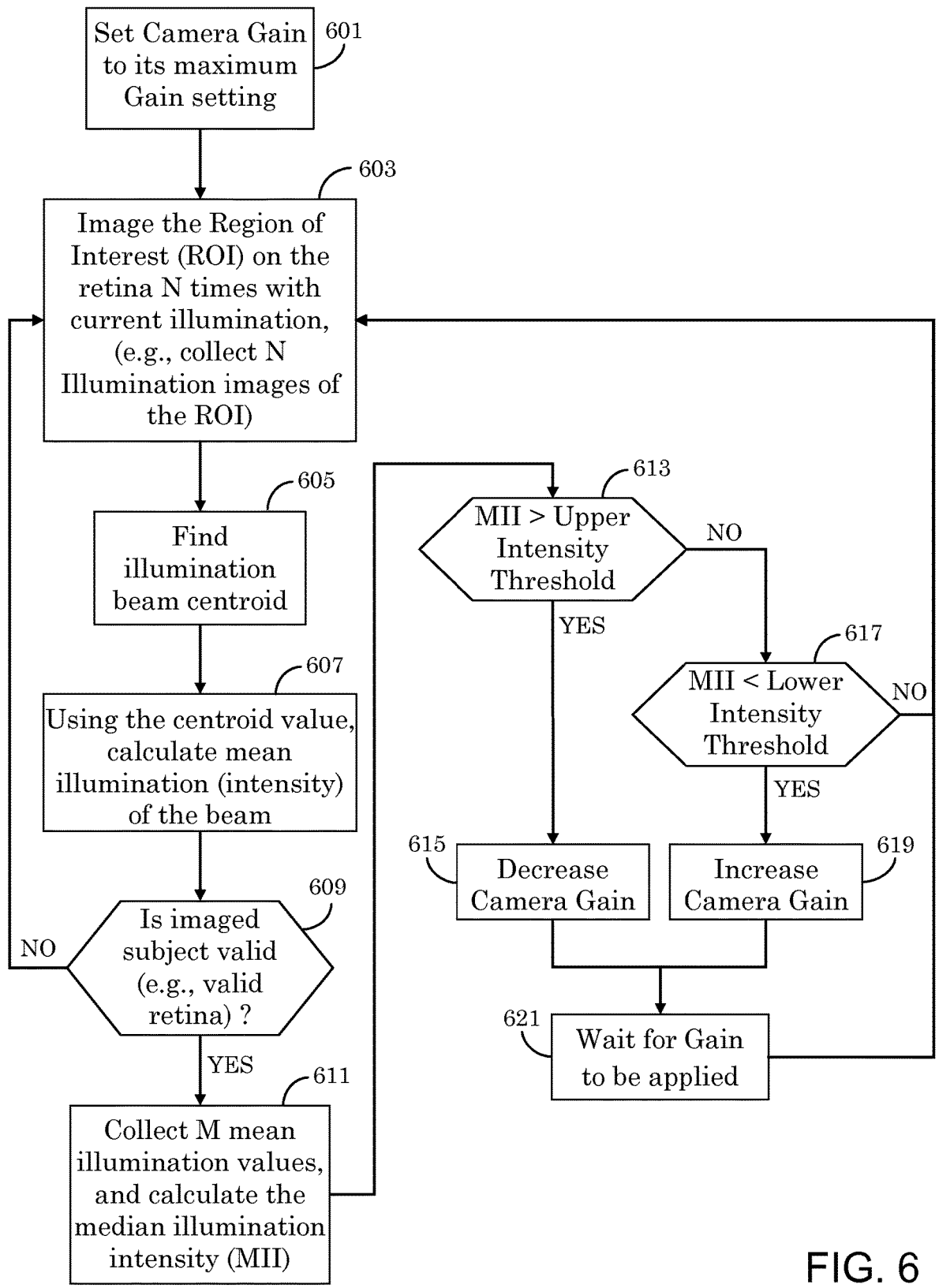
FIG. 6 illustrates an example embodiment of an auto-brightness adjustment method for a camera in accord with the present invention.

FIG. 6 illustrates an example embodiment of an auto-brightness adjustment method for a camera in accord with the present invention. The present embodiment is described within the context of a retina camera within a slit scanning ophthalmic system, but it is to be understood that the present invention may be extended to other types of ophthalmic imaging systems. As explained above, in a slit scanning ophthalmic system, an illumination slit is scanned across the retina (or fundus), and a slit-image is collected at each scan location to construct a full-frame image. This scanning process may be continuously repeated to collect a series of full-frame images, such as in a live imaging stream or video feed. For ease of implementation, one of the scan locations within a scanning sweep across the retina may be designated the region of interest (ROI) (or FOV of interest) of the retina on which gain control will be based. For example, a central area of the retina roughly corresponding to the area covered by an illumination slit at the center of the retina may be selected as the ROI. It is to be understood that any other area, or slit location, on the retina may be selected as the region of interest. By selecting a specific slit location as the region of interest, a "ROI-image" (e.g., data from a slit-scan position corresponding to the region of interest at a given illumination can be collected, also termed an "Illumination image") may be obtained during each scanning sweep (or during a fly-back sequence of the scanner between scanning sweeps). A number, N, of valid ROI-images (e.g., illumination data) are collected on a continuous basis at the given region of interest on the retina. For example, in a live video feed from the retina camera, a ROI-image corresponding to each video frame in the video feed may be collected. The collected ROI-images are analyzed. Any collected ROI-image that is not part of the retina (e.g., the target subject to be imaged) is designated as "not valid" and not used for automatic gain control, and the remaining (valid) ROI-images are analyzed to determine if the gain on the retina camera needs to be changed (e.g., increased or decreased). The workflow is as follows:

1. When the operator elects to start a scan, the gain of the retina camera is set to a predefined starting value and the scan starts (step 601). For example, the starting value of the camera gain may be set to its maximum.
2. Collect N ROI-images (illumination-strip data corresponding to a given region of interest on the retina, e.g., "Illumination images"), step 603. This data may be continuously collected during a live feed from the retina camera (e.g., in a preview mode) so as to continuous adjust its gain in anticipation of a fundus image capture sequence.
3. Find the beam centroid of each ROI-image (step 605). The centroid may correspond to the brightest region (e.g., region of highest intensity) of a ROI-image.
4. Calculate the mean beam illumination on the retina using the centroid as a guide to where the beam illumination is on the retina (step 607).
5. Check to see if this data appears to be from the target subject to be imaged (e.g., the retina), step 609. This may be achieved by determining if the data meets minimum conditions for an autofocus operation and/or meets a minimum signal-to-noise (SNR) ratio. For example, if no eye is present, then the SNR of the data will below a minimum threshold, and it can be designated as not valid. If the data has sufficient SNR, then the system can attempt an autofocus operation (e.g., using the centroids). This autofocus operation may use, for example, the method outlined in International Application No. PCT/EP2018/058138, herein incorporated in its entirety by reference. This approach may attempt to align the centroid with a reference bar or with another centroid signal. If the centroid is not defined well enough to achieve alignment, e.g., if the autofocus fails, then the data may be designated as not valid. Alternatively, or in addition, the iris cameras may be used to determine when the collected data should be designated as not valid. For example, if the iris camera identifies conditions that may interfere with the capturing of the fundus (e.g., an eye blinked or eye movement beyond a predefined threshold), the data may be designated as not valid. If the data is designated as not valid, then it is not used for gain control and processing returns to step 603.

6. In step 611, a number M of these average illuminations (from step 607) are collected and the median of the collected average illuminations is calculated. For example, step 611 may be a running median calculation, wherein each newly determined average illumination (from step 607) is incorporated into a median calculation (of the M most recent average illuminations). Alternatively, the system may accumulate M average illuminations to determine their median.

7. In step 613, if this median illumination from step 611 is greater than an upper intensity threshold (and greater than the minimum gain of the retina camera), then the gain of the retina camera is decreased in step 615 (e.g., by a first predefined discrete step). However, if the median illumination is not greater than the upper intensity threshold, then processing flows to step 617.

8. In step 617, if the median illumination from step 611 is less than a lower intensity threshold (and less than the maximum gain on the retina camera), then the gain of the retina camera is increased in step 619 (e.g., by a second predefined discrete step). However, if the median illumination is not less than the lower intensity threshold, then processing flows back to step 603.

9. If a change in gain was made either in step 615 or step 619, then in step 621 the system waits for a predefined period (e.g., waits for this gain change to take effect) before returning to step 603. This workflow may run continuously while the patient is being imaged, but may restart if a given region of interest is changed by the user. In this manner, the intensity of preview images of the retina (e.g., a running stream of retina images) is continuously adjusted.

The user can change the area of the retina that is optimized (e.g., the ROI upon which camera gain is adjusted) by clicking on a new region of interest on the live imaging stream. This information is then used as an input to where in the received image (e.g., which strip-image(s) in a scanning sweep) to process for gain control. The workflow of gain optimization would remain the same as mentioned above, but with a different imaged area being analyzed. Optionally, in order to keep the live acquisition as fast as possible, the areas of the image that the user can select may be limited to a preset number of area zones within a full-frame image, or video frame. If the user clicks anywhere in one of these zones, the entire zone may be used for optimization, or optimization may be limited to a predefined region (e.g., illumination strip(s)) within the selected zone.

This auto-brightness adjustment can be combined with the auto-focus feature described in International Application No. PCT/EP2018/058138, to do a full image optimization prior to the acquisition of an image to ensure that the captured images are consistent and optimal. For example with reference to FIG. 3b, region 420 illustrates a focusing tool, wherein the system's focus is adjusting until a beam centroid 91 of an illumination beam 93 substantially lines up with a reference bar 92, which can, for example be determined by calibration. Alternatively, if an ROI is illuminated by two illumination beams, then focus may be adjusted until the two beams' respective beam centroids align. The auto-brightness feature would have significant value during FA and ICG imaging as the gain could be continuously changes during the different phases of imaging (e.g., wash-in and wash-out). Also, if the option to adjust the brightness was selectable by the user, the user could monitor certain regions of the retina without getting saturation during an FA movie.

Distortion Correction

As it would be understood, the fundus of an eye is curved, but fundus images are generally two dimensional (e.g., flat) images. Because fundus images are flat representations of curved surfaces, it is desirable to account for distortions in determining their projection. During this process, the raw image collected by the sensor is processed to create a distortion compensated image which can either be presented to the user or used in further processing such as registration and montaging. There are many ways to accomplish this, as would be known by one skilled in the art. In one embodiment, a model based approach is used, where the 2D data is mapped to a 3D model of the eye. In addition to accounting for distortions while projecting images, it is also desirable to account for them in making measurements, copying measurements and annotations between two images, and montaging images in case the images are not taken with the same fixation.

The first step in enabling compensation of the image for distortions inherent in the imaging process is to identify an anchor point. This can be the fovea or the optic disc or an arbitrary position. This can be enabled by identifying the fovea as the fixation position of the instrument. In an alternate embodiment, the user can select the anchor point, or a feature in the image such as the fovea that can be used as an anchor point. In an alternate embodiment, the anchor point can be selected by automatically identifying a feature of interest in the image such as the fovea or optic disc.

Figure 7:
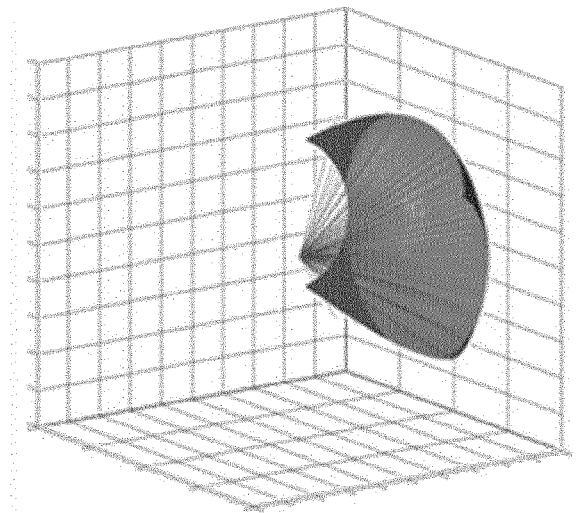
FIG. 7 illustrates a conceptual three-dimensional (3D) sphere (or partial sphere), which may represent the curvature of the fundus of an eye.

FIG. 7 illustrates a conceptual three-dimensional (3D) sphere (or partial sphere), which may represent the curvature of the fundus of an eye. After the anchor point is identified, the images can be projected onto a conceptual 3D sphere (such as illustrated in FIG. 7), using an inverse projection that describes each image pixel via a 3D unit ray vector. This approach requires knowledge of the system's optical distortion. In one embodiment, this distortion can be represented with a radially-symmetric polynomial. It is often convenient to encode the ray angle as a unit vector (e.g., (l, m, n)=(cos ϕ sin θ, sin ϕ sin θ, cos θ)). These unit vectors place the pixels and their image data onto the unit sphere. The co-ordinates (x, y) on the sensor are then given by $$\begin{bmatrix} x \\ y \end{bmatrix} = \begin{bmatrix} l \\ m \end{bmatrix} \left( \frac{a + b\sin^2\theta}{\sin(v)} \right)$$

where θ is the angle from the center of the field of view and v is the field-of-view half-angle $\vec{l}\vec{m}(\vec{l}, \vec{m}, \vec{n})$. Parameters "a" and "b" may be empirically set as a=1.06 and b=−0.15, as these values give a good approximation of the lens distortion. One could also use a model that accounts for the shape of the eye if this is known. The images can be aligned on the sphere in 3D according to their relative fixation positions. A map between the projected image's 2D pixel coordinates and its coordinates in 3D inverse projected space is constructed as a result of the algorithm.

To enable anatomically-correct measurement, ophthalmic imaging systems may incorporate data that reverses the projection with the images it exports. One method to overcome this challenge is to store, beside the original 2D image, three 2D arrays containing the x, y, and z coordinates of each point in the original image. An alternate embodiment stores 3D positions in an array with the 2D coordinates of each position in the 2D image. This methodology is included with the Digital Imaging and Communications in Medicine (DI-COM) standard Wide Field Ophthalmic Photography Image Module. This methodology may suffer from performance issues as the amount of data to be stored and managed may be large, which is especially the case in high resolution imaging. In an alternate method to compensate for this issue, the system stores only the coordinates of any measurements performed. Alternatively or in combination, a model is stored which can be run on an arbitrary set of 2D positions to generate the relevant 3D position. This has the additional benefits of allowing the model to be improved upon after the data has been collected and stored or even customized to the imaged eye in the future.

Montaging Considerations

As previously mentioned, the optics of the system determines the maximum field of view of the system. In one embodiment of a slit scanning ophthalmoscope, a rectangular line of illumination with an aspect ratio of about 30:1 is used to capture a single image with a FOV of 90° per ISO Standard 10940. If it is desirable to extend beyond this field of view, it is possible to change the rotation of the eye relative to the instrument, capture another image, and montage the resulting images. The easiest way to adjust the rotation of the eye relative to the system is to adjust the fixation of the eye. This can be accomplished by adjusting the location of the fixation target in the system. Montages of fundus images can aid clinicians by providing a more complete view of the retina. Fundus image montaging is a common technique for extending the imaged field-of-view (FOV), and has been offered as a feature on fundus cameras. Techniques for montaging wide field-of-view fundus images are described in U.S. Pub. No. 2017/0316565, the contents of which are hereby incorporated by reference in their entirety.

Figure 8:
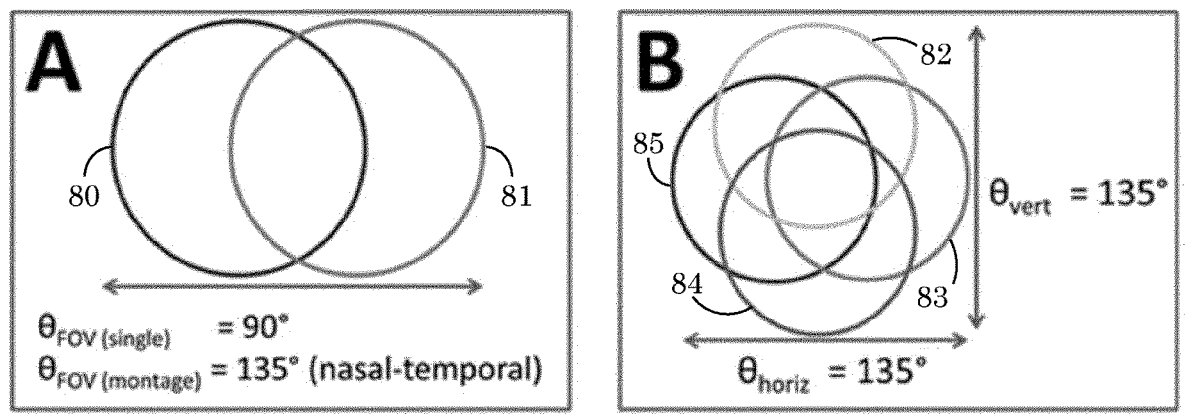
FIG. 8 illustrates examples of two acquisition patterns to collect multiple images that can be stitched (e.g., montaged) to provide a larger field of view.

FIG. 8 illustrates examples of two acquisition patterns to collect multiple images that can be stitched (e.g., montaged) to provide a larger field of view. Box A in FIG. 8 shows two different images 80 and 81 stitched together to achieve a 135° field-of-view in the horizontal dimension. Box B in FIG. 8 shows four images 82, 83, 84, and 85 collected to create an image achieving a 135° field-of-view in both horizontal and vertical dimensions. The appearance of the final montage can be improved by choosing appropriate regions of transition between the images, and performing blending only in the vicinity of a particular seam at these transitions, rather than throughout the entire region of overlap. Seam-finding algorithms attempt to produce a cut through the overlap region that results in the best-looking blended montage.

There are multiple possibilities for selecting the area of overlap and the area of transition (seams). Examples include identifying seams that minimize the differences between scans at the seam and choosing among the geometric boundaries of the images. Indicating which image has contributed to a montage is sometimes done by drawing lines on top of the montaged image, but many times montages are presented without any indication how the constituents contributed to the final image. It is desirable to find a boundary that is not one of the edges, but instead identifying important features such as the fovea or the optic nerve head, and not picking a boundary that cuts through these key features. The processor could identify in which image key features are best visualized and therefore use more of that image for montaging. In another embodiment, a user could have the option of adjusting the seams to select more of one image and less of another image for montaging purposes.

Figure 9A:
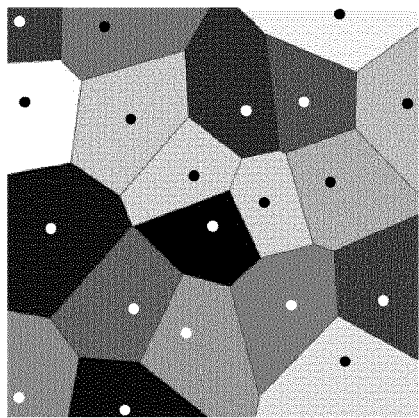
FIG. 9*a* illustrates an exemplary Vornonoi diagram, which is a portioning of a plane into regions based on distance to points in a specific subset of the plane.
Figure 9B:
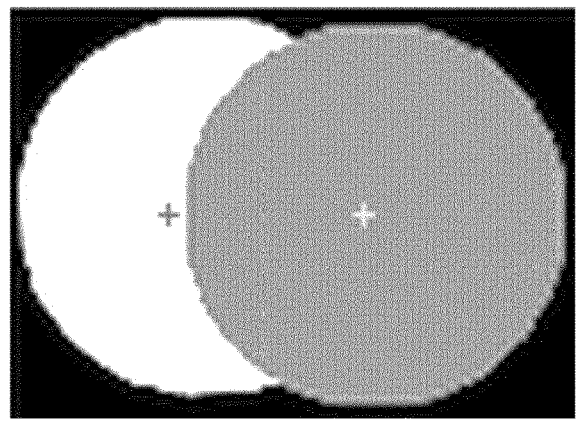
FIG. 9*b* shows a Voronoi diagram representing two montaged images with crosshairs at their respective, center seed positions.
Figure 9C:
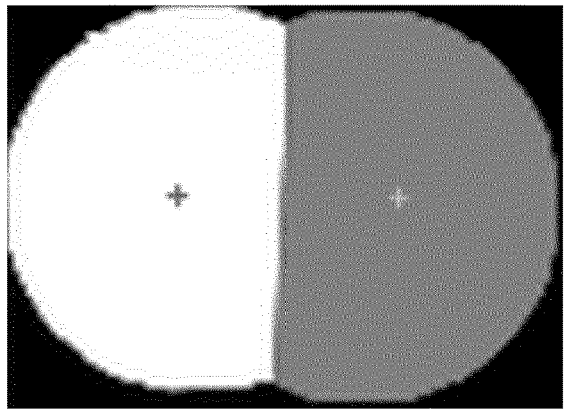
FIG. 9*c* illustrates the pixel contribution from each image in the two image montage case, as illustrated in box A of FIG. 8.
Figure 9E:
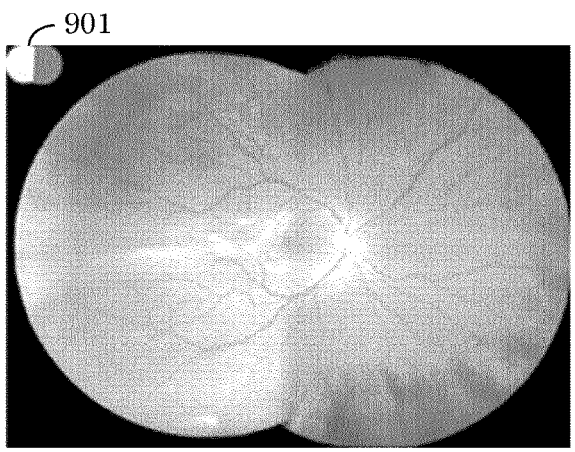
FIG. 9*e* shows a montaged image for a two image case.
Figure 9D:
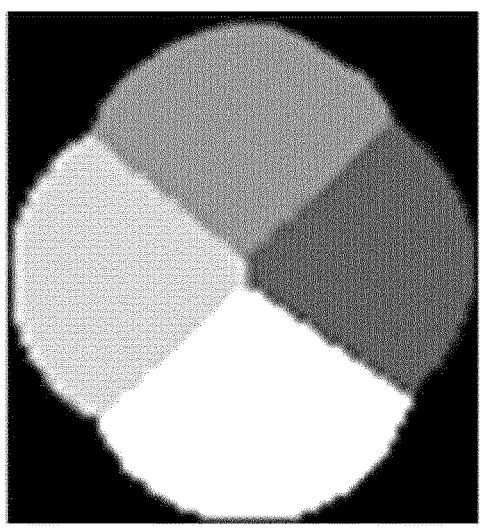
FIG. 9*d* illustrates pixel contribution from each image in the four image montage case, as illustrated in box B of FIG. 8.
Figure 9F:
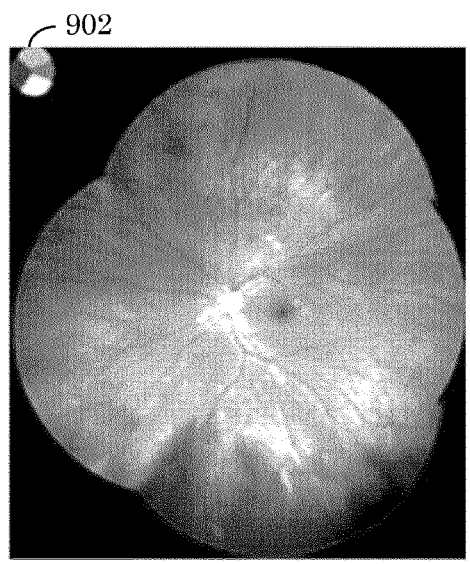
FIG. 9*f* shows a montage images for a four image case.

FIG. 9a illustrates an exemplary Voronoi diagram, which is a portioning of a plane into regions based on distance to points in a specific subset of the plane. The set of points (called seed, sites, or generators) is specified beforehand, and for each seed there is a corresponding region consisting of all points closer to that seed than to any other. These regions are called Voronoi cells. The use of Voronoi diagrams for montaging has been proposed (see for example Laraqui et al., "Image Mosaicing using Voronoi diagrams" DOI: 10.1007/s11042-016-3478-z). Its use in montaging fundus images is herein described. For fundus image montaging, the seed points are the center points of each image being montaged. For example, FIG. 9b shows a Voronoi diagram representing two montaged images with crosshairs at their respective, center seed positions. With the center point as the seed, for each pixel in the final montage, the pixel from the image whose center is closest is selected. FIG. 9c illustrates the pixel contribution from each image in the two image montage case, as illustrated in box A of FIG. 8. FIG. 9e shows an example montaged image in a two image case. FIG. 9d illustrates pixel contribution from each image in the four image montage case, as illustrated in box B of FIG. 8. FIG. 9f shows an example montaged image in a four image case. A small overlap between images is allowed and blending of the images is carried out in this overlap region. Blending creates more natural-looking transitions between images in the final montage, by mitigating differences in illumination and/or vignetting among the overlapping parts of the constituent images. To aid the instrument user, along with the montaged image, a schematic (e.g., montage icons 901 and 902) illustrating where the seams are located in the montaged image and which components (images) contribute to which portion of the montaged image is presented. Generally, the montage image schematics or icons (901 and 902) indicate the boundaries of the partially-overlapping fundus images that make up the montaged fundus image. In other words, the montage icons (901 and 902) generally depict the outer perimeter shape of their respective montaged image, and are divided into sectors with each sector corresponding to an individual (contributing) image in the montaged image, and the shape of each sector generally depicts the portion of its corresponding image that is contributed to the montaged image.

Performance Enhancements

Ophthalmic images may be high resolution images, such as 4K×4K, and such large files can have a noticeable impact on file manipulation operations, such as image loading and image processing (including distortion correction and montaging as described above, along with other more typical image processing such as adjustments in brightness, contrast, saturation, gamma, sharpness, etc.). On the other hand, viewports on a computer screen, on which loaded images are rendered (displayed), are generally of much lower resolution, such as 0.3K by 0.3K. This difference may result in less than optimal performance in typical image rendering operations, such as loading an image onto a viewport, or viewport zooming and panning. For example, an image is typically loaded only when it is selected for review, and any needed image processing is typically not applied until the image is called for review (e.g., to be rendered/displayed) in a viewport, such as illustrated in FIG. 3d. This needed image processing may include, for example, distortion correction and/or montaging. Typically, the loaded image (at full resolution) is resized to the viewport resolution for display (e.g., by the computer's operating system or other display API, e.g., Application Programming Interface). Similarly, in a zooming operation, a loaded image (or a select portion of the image) is resized for display according to the zooming factor. Consequently, one generally does not have a pixel-to-pixel correlation between a loaded image and an image displayed on a computer screen. This can complicate onscreen measurements of displayed items. It is also noted that typically any image processing is applied at the full resolution of the loaded image, and the resultant, processed image is rescaled for display to the viewport. Additionally, when a currently loaded image is removed from a viewport (e.g., is no longer displayed), the current loaded image is removed from active memory, such that if the same image is later recalled, it will need to repeat the same loading, processing, and scaling process for display. Herein is presented a new scheme for enhancing performance that provides for better response times in regards to image processing (e.g., brightness, contrast, saturation, gamma and sharpness) along with less memory consumption. Also presented are new zooming and panning features that are an outgrowth of this new scheme and designed to maximize performance.

Figure 10:
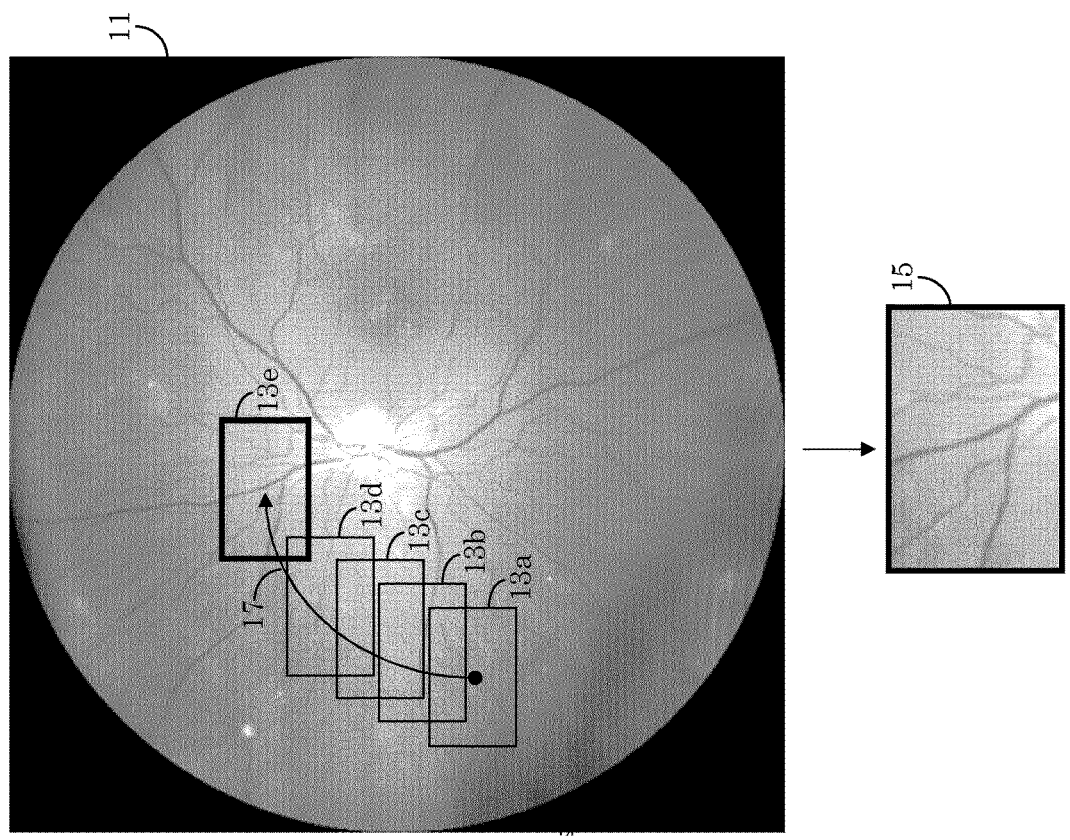
FIG. 10 illustrates a non-optimized, panning operation of a viewport across a loaded image of higher resolution.

As it would be understood, the loading of multiple large files places a high demand on active (e.g., working) memory capacity, but such large files can facilitate a typical panning operation, wherein a viewport is panned (or moved) across a loaded image. FIG. 10 illustrates a typical, non-optimized, panning operation of a viewport across a loaded image of higher resolution than the viewport. Image 11 is loaded at full resolution, and rectangles 13a to 13e represent the panning movement of a viewport 15 across image 11. That is, viewport 15 illustrates what is displayed on a computer screen, and the size of viewport 15 defines the size of rectangles 13a to 13e. The portion of image 11 within one of the rectangles 13a to 13e defines what is displayed on a computer screen via viewport 15. In the present example, rectangle 13a represents the initial position of viewport 15, rectangle 13e represents the final position of viewport 15, and arrow 17 represents the panning motion of viewport 15 from rectangle 13a to rectangle 13e across image 11.

The following are performance enhancements that compensate for some of the difficulties described above. For example, it has been found that the present performance enhancements reduced initial image loading time by about 80%, reduced memory capacity requirements by about 30%, reduced some image processing times to the point where they were imperceptible by a user, and substantially maintained a 1-to-1 resolution (or close to pixel-to-pixel) match between a displayed image and a loaded image in working memory.

Firstly, the present embodiment may implement various stages of image pre-fetching. For example, the present ophthalmic device may automatically fetch images in a background thread for images in a Today list (see for example, patient information screen 350 of FIG. 3a), irrespective of whether any images have been selected for viewing. For example, images associated with a patient in the Today list (e.g., selected patient 355) may be loaded in the background prior to any analyze option (356) or acquire option (357) being selected. Optionally, images may be loaded from most recent to oldest. Further optionally, this pre-fetching may be limited to images taken today and a predefined number (e.g., one or two) of the most recent previous doctor visit by the same patient. Pre-fetching may also be applied at the acquire stage (see for example acquisition screen 345 in FIG. 3b). For example, as each image is acquired (e.g., captured), as listed in area 365, the acquired images are pre-fetched (e.g., loaded) and processed (e.g., image corrected) for display. Pre-fetching may also be applied at the review stage (see for example, Proofsheet display 330 of FIG. 3c). As explained above, Proofsheet display 330 shows thumbnails 370 of images collected for a particular patient, and an operator selects images for further analysis from this collection. As each image is selected, thumbnails of the selected images are placed in Selection Bin 371. Optionally, pre-fetching can begin as soon as the operator reaches Proofsheet display 330 and before any thumbnails are selected by the user. That is, the present ophthalmic device may pre-fetch (and apply distortion correction) to the entire collection of images represented by thumbnails 370, from most recent to oldest. However, user-selected images, as identified by Selection Bin 371, may be assigned a higher priority for loading and distortion correction.

As is explained more fully below in section "Auto-Discovery and Data Synchronization" the present ophthalmic device may be part of a network of multiple similar ophthalmic devices, different medical equipment, databases, etc. Additionally, an individual ophthalmic device may not have all patients' data (e.g., images) within its internal memory. Therefore, an ophthalmic device may request and retrieve copies of a patient's images from other ophthalmic devices on the network as part of this pre-fetching operation.

As each image is loaded, it is optionally distortion corrected (or otherwise imaged processed), as explained above, and made the base of an image pyramid. Each image pyramid includes multiple copies of its based image in order of decreasing resolution. The original loaded image may be discarded. That is, rather than storing the pre-fetched images, multiple copies of each pre-fetched, and optionally distortion corrected, image are stored as a corresponding set (within the ophthalmic device) at various reduced resolutions in an image cache. Each set of images may constitute an image pyramid.

Figure 11:
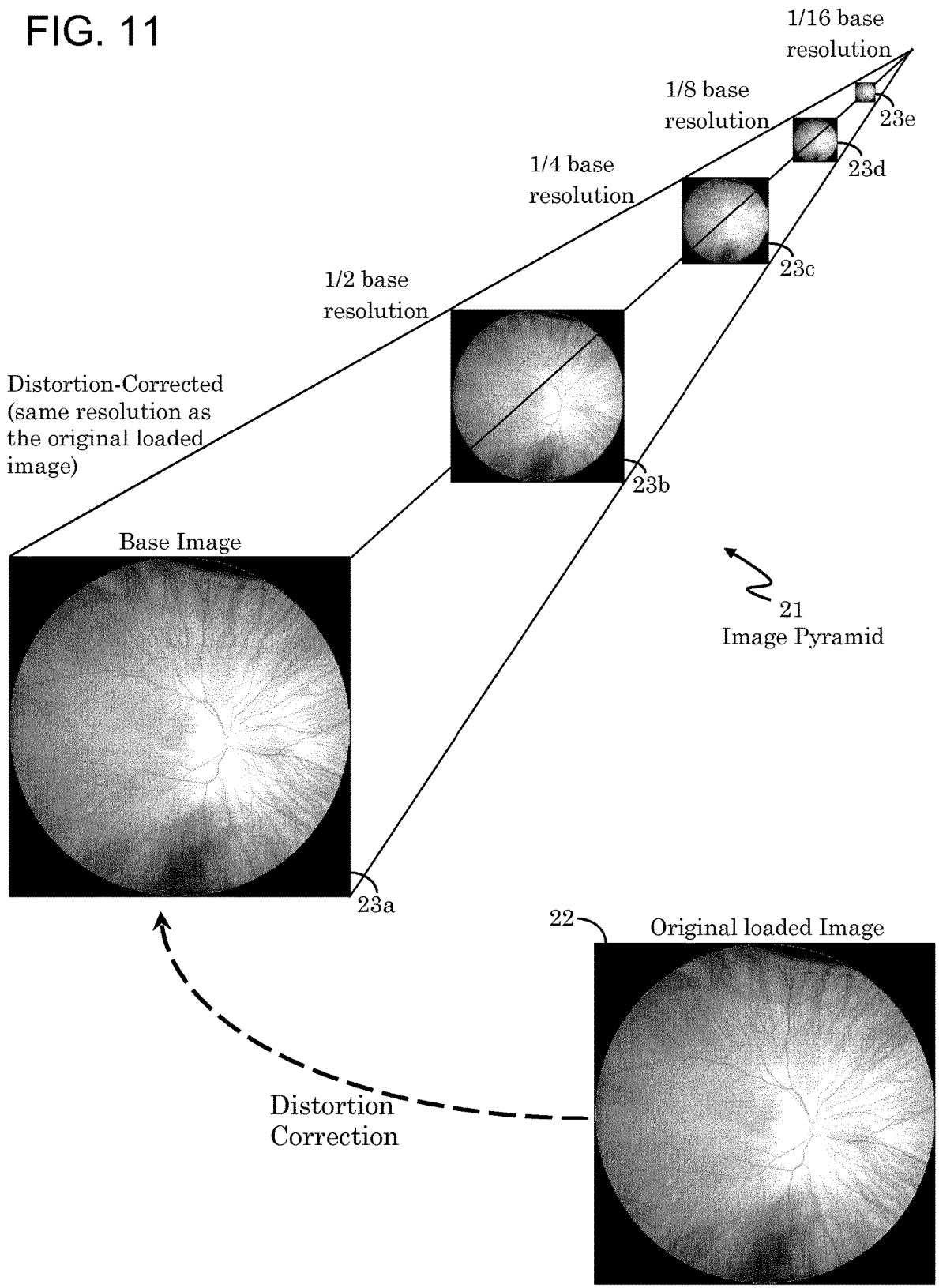
FIG. 11 illustrates an example of creating an image pyramid from a pre-fetched (or loaded) image.

FIG. 11 illustrates an example of creating an image pyramid 21 from a pre-fetched (or loaded) image 22. The image pyramid 21 includes a base image 23a and multiple reduced resolution copies (e.g., 23b to 23e) of the base image 23a for storage into an image cache. The image cache may be maintained in short term memory (e.g., active memory such as DRAM or SRAM) or in long term memory (e.g., a hard drive or solid state drive). Optionally, the base image 23a (e.g., starting image, or highest resolution image in image pyramid 21) may have a resolution matching that of the loaded image 22. Alternatively, the base image 23a may have a substantially predefined resolution (e.g., number of pixels in an image) of, for example, 2K×2K irrespective of the native resolution of the loaded image 22. If base image 23a has a predefined resolution, then the loaded image 22 may be resized to the predefined resolution. For example, if the loaded image 22 has a higher resolution than the predefined resolution (e.g., loaded image 22 is of 4K×4K, 6K×6K, or 8K×8K), the loaded image 22 may be resized (e.g., downsampled) to substantially match the predefined resolution of base image 23a. In a presently preferred embodiment, however, and as depicted in FIG. 11, the resolution of base image 23a is defined by (e.g., made equal to) the resolution of the loaded image 22. In this manner, when a viewport displays a maximum zoom, the highest resolution image available (e.g., the resolution of the loaded image 22) will be used to provide the best zoom resolution, as is explained more fully below. In either case, any needed image preprocessing (such as distortion-corrected for curvature of the eye) may be applied to the loaded image 22, and the resultant corrected image be used to define the base image 23a. In this manner, not only the base image 23a, but all lower resolution copies 23b to 23c also, will be distortion corrected (e.g., preprocessed) and ready for display. This reduces the time required to load an image onto a view port when loading from the image pyramid 21, since this avoids having to re-apply distortion correction every time an image is loaded for display. Optionally, at each resolution-reduction step in image pyramid 21, each image copy reduces the resolution of its base image (or of its most previous-step image copy) by a predefined fraction, e.g., in ½ or ¼. Distortion correction (and other image preprocessing) that would typically be applied to the loaded image 22 in preparation for display can instead be applied to all the images 23a-23e in image pyramid 21, and the distortion corrected image pyramid 21 can be stored in the image cache for later access. The loaded image 22 may be discarded. In this manner, each loaded image 22 is replaced by a corresponding image pyramid 21.

In operation, when a user selects an image for rendering via a viewport of a given resolution, the resolution of the viewport is compared with the different resolution copies in image pyramid 21 that corresponds to the user-selected image. The copy with the closest, but higher, resolution to the viewport is selected for loading into the view port. It is not necessary to apply any distortion correction, as would be the case in the typical case, since the stored image copies are already distortion corrected, as explained above. Furthermore, although loading an image into a viewport typically requires additional image processes specified by the viewport (e.g., brightness, contrast, saturation, gamma, sharpness, etc.), because the selected image copy from the image pyramid will likely be of much lower resolution than the original loaded image 22, this additional image processing can be accomplished in much less time than typical. These features greatly reduce the time needed to load an image into a viewport.

FIG. 12 illustrates the displaying of an image with zero zoom. In the present example, square 31 represents a viewport, and image 33 is the selected image from an image pyramid having a resolution (e.g., size) closest to, but higher, than the viewport 31. Frame 35 represents viewport 31, and it indicates the portion of image 33 that should be rendered within viewport 31. In embodiments, prior to rendering an image in viewport 31, the loaded image 33 undergoes a cropping stage to define a cropped image 37. Since frame 35 encompasses the entirety of image 33, however, cropped image 37 is a full copy of image 33. The cropped image 37 is then resized to match the resolution of viewport 31 for rendering.

FIG. 13 illustrates a zoom operation in accord with some embodiments. In the present example, frame 35 again indicates the portion of image 33 that should be rendered within viewport 31. However, since image 33 is of higher resolution than viewport 31, the zooming operation basically defines a cropping area for cropped image 37. Again, the resolution of cropped image 37 is resized to match that of viewport 31 for rendering, if needed. If the user were to zoom in further to a point that surpasses the resolution of image 33, then the image 33 would be replaced with another image from the image pyramid whose resolution is closest to, but higher, than the current zoom value, and the present rendering sequence would be applied to the newly loaded image.

Figure 14:
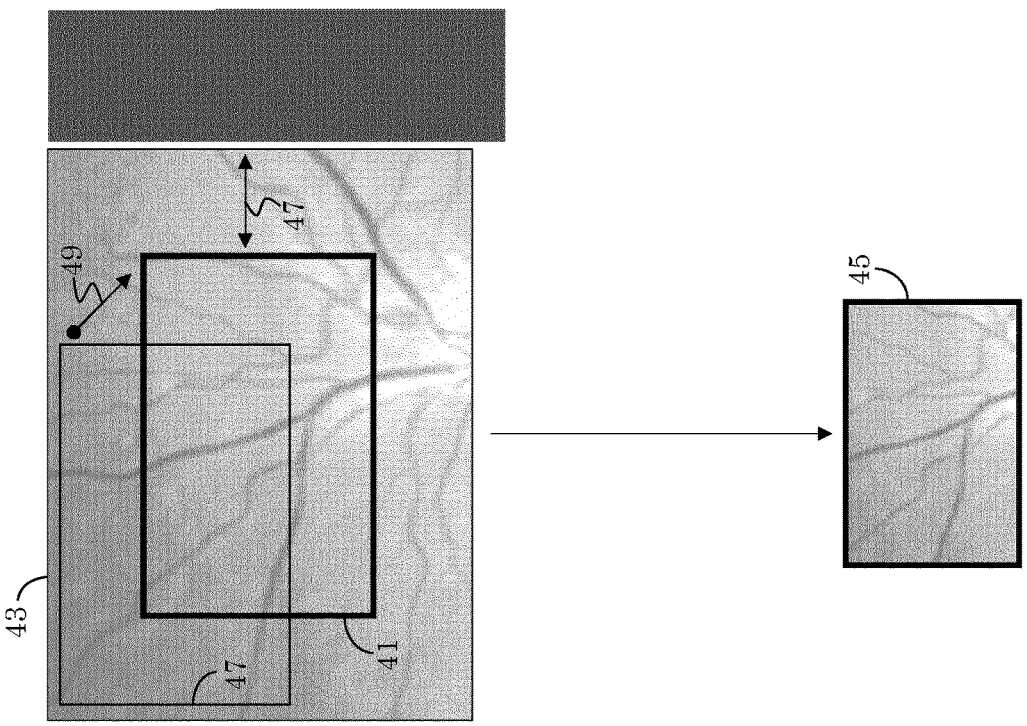
FIG. 14 illustrates a panning operation in accord with some embodiments of the present invention.

FIG. 14 illustrates a panning operation in accord with some embodiments of the present invention. In a panning operation, a cropped image 43 larger than the viewport 45 is created. In the present case, frame 41 within cropped image 43 represents viewport 45. The larger size of cropped image 43 creates a buffer zone 47 in which frame 41 may move. For example, rectangle 47 may represent an initial position of frame 41 in a panning motion, as represented by arrow 49. As it would be understood, cropped image 43 may be much smaller than the original loaded image, as represented by image 11 in FIG. 10. That is, cropped image 43 is cropped from a lower resolution image (e.g., selected from an image pyramid as explained above) than the original image, and thus places much lower memory capacity requirements on the system. If frame 41 were moved beyond the boundary of cropped image 43, then cropped image 43 would be replaced with a new cropped image with another buffer zone to continue the motion of frame 41. For example, if frame 41 is moved to within a predefined distance threshold from a boundary of cropped image 43, then a new cropped image may be loaded to replace cropped image 43 in anticipation of frame 41 moving beyond the boundaries of cropped image 43.

Auto-Discovery and Data Synchronization

Often times, based on their patient caseload, clinicians will have the need for more than one of the same ophthalmic instrument or may wish to review data from one type of imaging instrument on another type of instrument. It is desirable for the instruments to be able to access the data collected on another instrument to facilitate data comparison over time. One way to accomplish this is to manually copy data from one instrument to another using a portable storage device (e.g. thumb or flash drive). Obviously this is time consuming and cumbersome as the number of instruments increases. Central servers are used for some clinics, where data collected on all the instruments on a network can be stored and accessed. This adds cost to the clinic and the data could be unavailable if the server is down or the network is not accessible. Electronic medical record (EMR) or picture archiving and communication system (PACS) software can be purchased where data is stored in a central repository either on a server or in the cloud by a third party. Again, data is only available when the network and third party's servers are operational and cost is added to the clinic.

Here, an approach where patient data is updated asynchronously on multiple instruments is described. With this approach, a patient does not have to wait for the instrument that was used on a previous visit to become available in order to gain access to images taken on the previous visit. Since the patient data is updated on all of the instruments, future acquisition and analysis is available on any instrument. The approach described herein could apply to two (or more) of the same type of ophthalmic diagnostic instrument (e.g., two slit scan fundus imagers) or two (or more) different ophthalmic instruments sharing a common software element (e.g., a fundus imager and an optical coherence tomography system both made by the same manufacturer and therefore having a common protocol). The two instruments could be in the same physical location or office, or could be distributed between multiple offices in a health system, but connected over a network.

Figure 15:
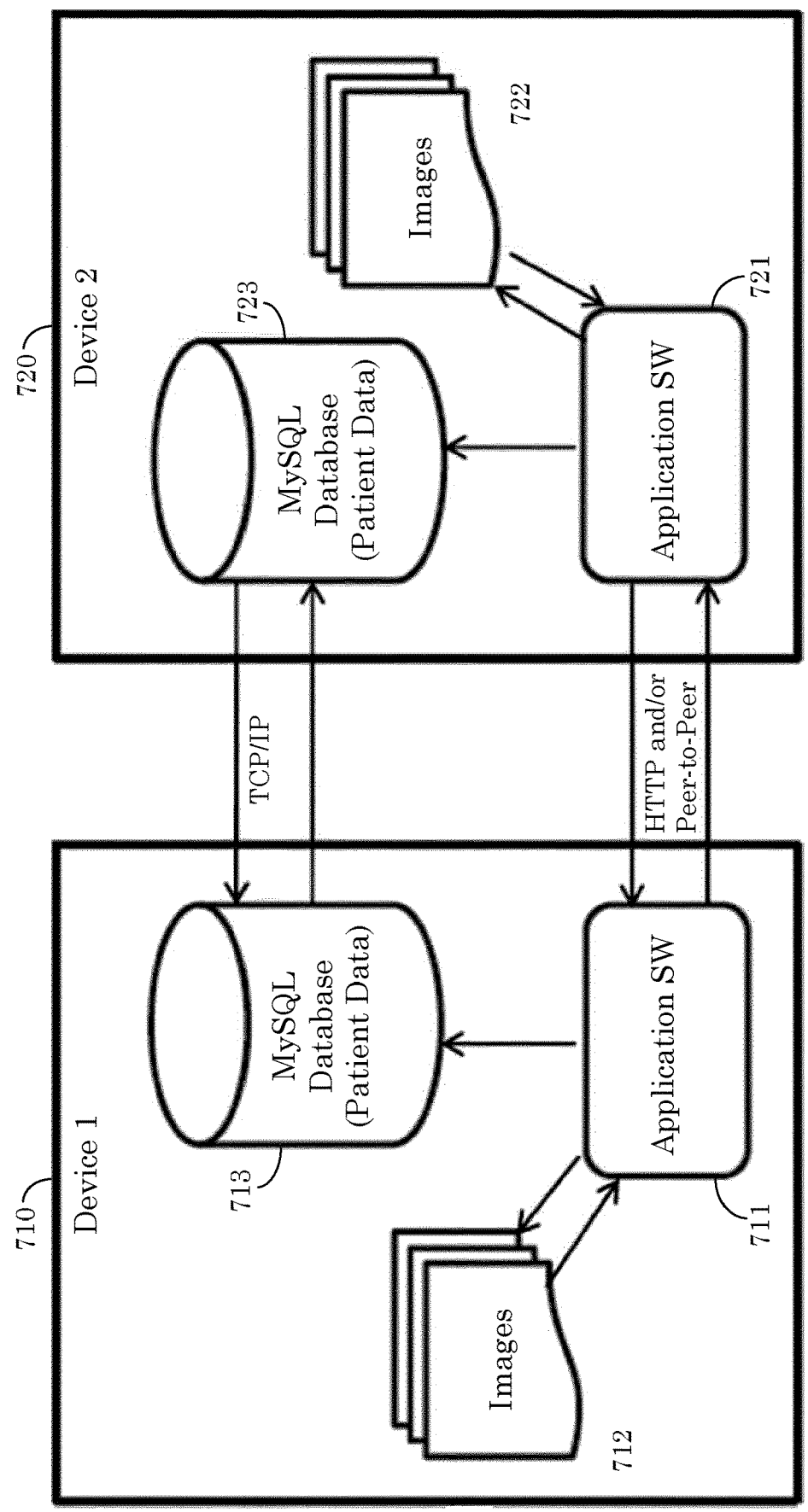
FIG. 15 schematically illustrates software and networking components of two ophthalmic diagnostic devices/systems.

FIG. 15 schematically illustrates the software and networking components of two ophthalmic diagnostic devices/systems. In the present embodiment, each device 710 and 720 contains application specific software 711 and 721, respectively, which contains different modules responsible for the basic operation and functionality of the instrument including initialization, data management, acquisition, review and analysis. Each device has its own database of images (712 and 722) or other type of diagnostic data that are collected with the device. In addition, each device has a patient database (713 and 723), e.g., MySQL, that is responsible for storing patient information including but not limited to, demographics, exam history, and image annotations and notes. The ophthalmic devices could be of the same modality or different modality (e.g., fundus imager or OCT). Within the present context, modality refers to a type of equipment used to acquire images of the body. Each system is connected to a local area network (LAN). Once connected, each system contains software which causes it to send out a signal over the network (e.g., a heartbeat signal indicating its existence on the network), in this particular embodiment, over the TCP/IP layer, which allows each system to automatically identify the presence of the other device for example using a proprietary broadcast membership protocol. All online ophthalmic diagnostic systems can build data structures about the other online members available in the local area network. It is possible for some LAN environments to block broadcast messages over TCP/IP. In this case, manual configuration of the devices could be carried out so that the devices can communicate with each other.

Once a device knows about the presence of the other devices on the network, it can establish a link between the patient databases 713/723 on each device to perform synchronization of the patient data. For example, the database synchronization for ophthalmic diagnostic devices can be achieved by using MySQL multi master replication. This is the process of establishing data consistency between device databases, such as for example, by automatically copying changes back and forth. Harmonization of the data over time is performed continuously. This involves actions to pull and apply (e.g., push) data changes from source (master) device to destination (slave) device. Two or more devices in which their databases are synchronized with each other are termed a synchronization group. Every ophthalmic diagnostic device acts as both master (to provide, or push, data to others) and slave (to pull changes from other devices). The database synchronization can happen in the background, and the application software 711/721 need not be aware of the replication. In the embodiment described herein, the image data 712/722 would not be automatically copied and remains on each individual device. Image data may be transferred from one device to another only when a particular patient data record is accessed on an instrument that lacks that patient's image data. Image data may be transmitted via a different layer of the network, e.g. HTTP or Peer-to-Peer. In alternative embodiments, the data could be stored on both instruments or on a central server. Optionally, to aid with this function, as part of the database synchronization, each device in a synchronization group may keep a record of which images are in which other device in the synchronization group.

Figure 16:
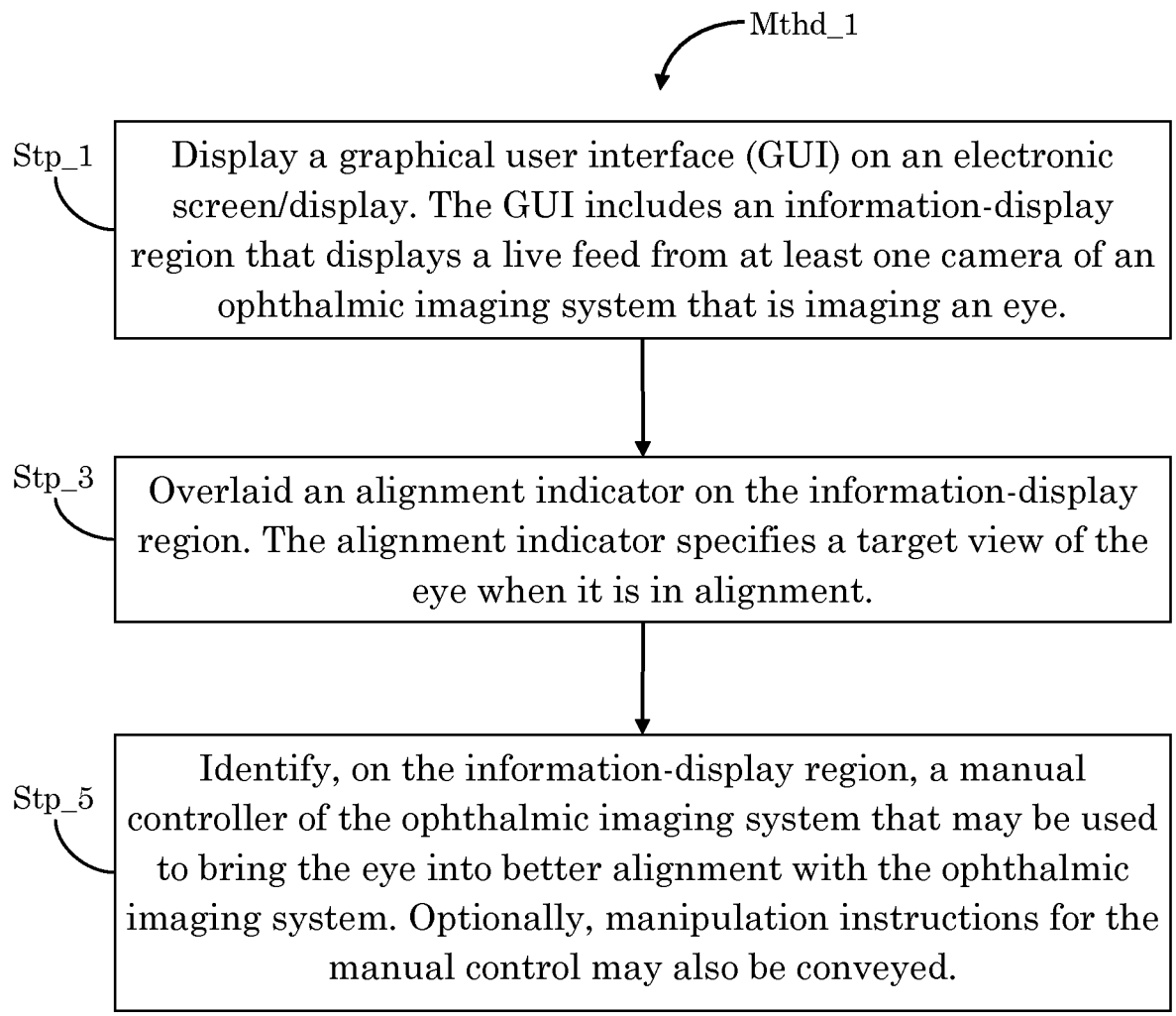
FIG. 16 illustrates an example method Mthd_1 for controlling an ophthalmic imaging system.

FIG. 16 illustrates an example method Mthd_1 for controlling an ophthalmic imaging system. Although this disclosure describes and illustrates particular steps as occurring in a particular order, this disclosure contemplates any suitable steps of the method occurring in any suitable order. In step Stp_1, a graphical user interface (GUI) is displayed on a computer screen, or other electronic display. The GUI includes an information-display region that displays a live feed from at least one camera of an ophthalmic imaging system imaging an eye. In step Stp_3, an alignment indicator specifying a target view of the eye when it is in alignment is overlaid on the information-display region. In step Stp_5, a manual controller of the ophthalmic imaging system is identified on the information-display region. The identified manual controller is operable by a user to improve alignment between the camera and the eye. The manual controller may be identified by one or more of text, visual depiction, and/or animation. Manipulation instructions (of the manual controller) for bringing the eye into better alignment with the system may also be conveyed on the information-display. Optionally, the manual controller and its manipulation instructions may also be conveyed audibly.

Figure 17:
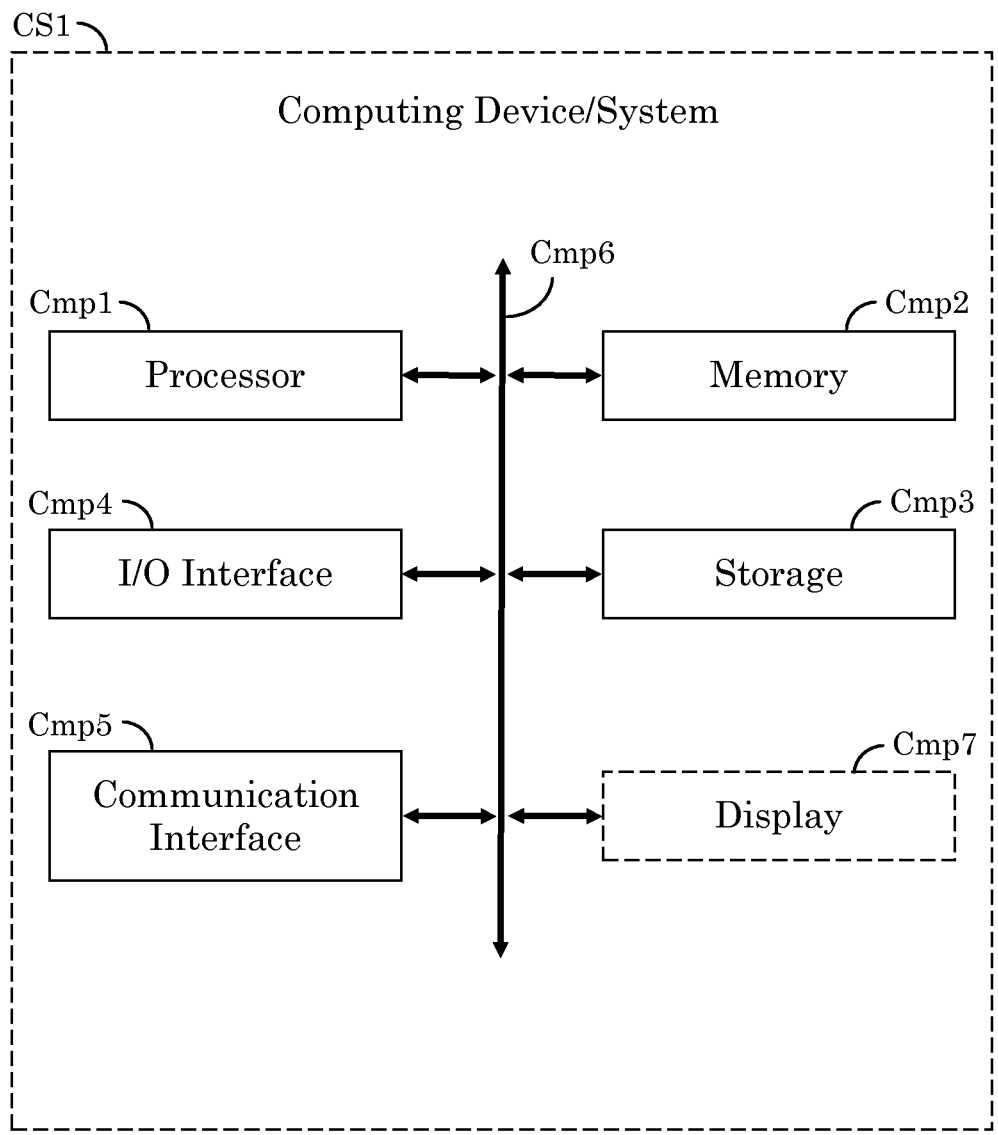
FIG. 17 illustrates an example computer system

FIG. 17 illustrates an example computer system (or computing device or computer device) CS1. In some embodiments, one or more computer systems CS1 may provide functionality described or illustrated herein perform one or more steps of one or more methods described or illustrated herein. The computer system may take any suitable physical form. For example, the computer system may be an embedded computer system, a system-on-chip (SOC), a single-board computer system (SBC) (such as, for example, a computer-on-module (COM) or system-on-module (SOM)), a desktop computer system, a laptop or notebook computer system, a mesh of computer systems, a mobile telephone, a personal digital assistant (PDA), a server, a tablet computer system, an augmented/virtual reality device, or a combination of two or more of these. Where appropriate, the computer system may reside in a cloud, which may include one or more cloud components in one or more networks.

In some embodiments, the computer system CS1 includes a processor Cmp1, memory Cmp2, storage Cmp3, an input/output (I/O) interface Cmp4, a communication interface Cmp5, and a bus Cmp6. The computer system may optionally also include a display Cmp7, such as a computer monitor or screen.

Processor Cmp1 includes hardware for executing instructions, such as those making up a computer program. For example, processor Cmp1 may be a central processing unit (CPU) or a general-purpose computing on graphics processing unit (GPGPU). Processor Cmp1 may retrieve (or fetch) the instructions from an internal register, an internal cache, memory Cmp2, or storage Cmp3, decode and execute the instructions, and write one or more results to an internal register, an internal cache, memory Cmp2, or storage Cmp3. In particular embodiments, processor Cmp1 may include one or more internal caches for data, instructions, or addresses. Processor Cmp1 may include one or more instruction caches, one or more data caches, such as to hold data tables. Instructions in the instruction caches may be copies of instructions in memory Cmp2 or storage Cmp3, and the instruction caches may speed up retrieval of those instructions by processor Cmp1. Processor Cmp1 may include any suitable number internal registers, and may include one or more arithmetic logic units (ALUs). Processor Cmp1 may be a multi-core processor; or include one or more processors Cmp1. Although this disclosure describes and illustrates a particular processor, this disclosure contemplates any suitable processor.

Memory Cmp2 may include main memory for storing instructions for processor Cmp1 to execute or to hold interim data during processing. For example, computer system CS1 may load instructions or data (e.g., data tables) from storage Cmp3 or from another source (such as another computer system CS1) to memory Cmp2. Processor Cmp1 may load the instructions and data from memory Cmp2 to one or more internal register or internal cache. To execute the instructions, processor Cmp1 may retrieve and decode the instructions from the internal register or internal cache.

During or after execution of the instructions, processor Cmp1 may write one or more results (which may be intermediate or final results) to the internal register, internal cache, memory Cmp2 or storage Cmp3. Bus Cmp6 may include one or more memory buses (which may each include an address bus and a data bus) and may couple processor Cmp1 to memory Cmp2 and/or storage Cmp3. Optionally, one or more memory management unit (MMU) facility data transfers between processor Cmp1 and memory Cmp2. Memory Cmp2 (which may be fast, volatile memory) may include random access memory (RAM), such as dynamic RAM (DRAM) or static RAM (SRAM). Storage Cmp3 may include long-term or mass storage for data or instructions. Storage Cmp3 may be internal or external to computer system CS1, and include one or more of a disk drive (e.g., hard disk drive, HDD, or solid state drive, SSD), flash memory, ROM, EPROM, optical disc, a magneto-optical disc, magnetic tape, Universal Serial Bus (USB)-accessible drive, or other type of non-volatile memory.

I/O interface Cmp4 may be software, hardware, or a combination of both, and include one or more interfaces (e.g., serial or parallel communication ports) for communication with I/O devices, which may enable communication with a person (e.g., user). For example, I/O devices may include a keyboard, keypad, microphone, monitor, mouse, printer, scanner, speaker, still camera, stylus, tablet, touch screen, trackball, video camera, another suitable I/O device, or a combination of two or more of these. Communication interface Cmp5 may provide network interfaces for communication with other systems or networks. Communication interface Cmp5 may include a Bluetooth interface or other type of packet-based communication. For example, communication interface Cmp5 may include a network interface controller (NIC) and/or a wireless NIC or a wireless adapter for communicating with a wireless network. Communication interface Cmp5 may provide communication with a WI-FI network, an ad hoc network, a personal area network (PAN), a wireless PAN (e.g., a Bluetooth WPAN), a local area network (LAN), a wide area network (WAN), a metropolitan area network (MAN), a cellular telephone network (such as, for example, a Global System for Mobile Communications (GSM) network), the Internet, or a combination of two or more of these.

Bus Cmp6 may provide a communication link between the above mentioned components of the computing system CS1. For example, bus Cmp6 may include an Accelerated Graphics Port (AGP) or other graphics bus, an Enhanced Industry Standard Architecture (EISA) bus, a front-side bus (FSB), a HyperTransport (HT) interconnect, an Industry Standard Architecture (ISA) bus, an InfiniBand bus, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or other suitable bus or a combination of two or more of these.

Although this disclosure describes and illustrates a particular computer system having a particular number of particular components in a particular arrangement, this disclosure contemplates any suitable computer system having any suitable number of any suitable components in any suitable arrangement.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

The foregoing embodiments of the present subject matter have been presented for the purposes of illustration and description. It is not intended to be exhaustive or to limit the present embodiment of subject matter to the precise forms disclosed. Many modifications and variations are possible in light of the above teaching. As will be understood by those familiar with the art, the present subject matter may be embodied in other specific forms without departing from the spirit or essential characteristics thereof. Thus, while the invention has been described in conjunction with several specific embodiments, it will be evident to those skilled in the art that many further alternatives, modifications, and variations are apparent in light of the foregoing description, and the invention described herein is intended to embrace all such alternatives, modifications, applications and variations as may fall within the spirit and scope of the appended claims.

The invention claimed is:

1. A method comprising:
    displaying a graphical user interface (GUI) on a screen, the GUI including an information-display region that displays a live feed from at least one camera of an ophthalmic imaging system imaging an eye;
    overlaying, on the information-display region, an alignment indicator specifying a target view of the eye when in alignment; and
    displaying on the information-display region, an image of a manual controller of the ophthalmic imaging system operable by a user, and wherein the display includes information suggesting the appropriate manipulation of the manual controller to improve alignment between the ophthalmic imaging system and the eye.

2. The method of claim 1, wherein the manipulation information includes animating the graphic representation of the manual controller.

3. The method of claim 1, wherein the manipulation information includes arrows conveying movement of the manual controller.

4. The method of claim 1, further comprising:
    automatically activating an image capture sequence in response to a determination of the eye being aligned based at least in part of on a comparison of the alignment indicator and the live feed.

5. The method of claim 1, further comprising:
    determining a size of the pupil of an eye in the live feed, and automatically selecting one of a plurality of imaging modalities based on the determined size.

6. The method of claim 5, wherein the plurality of imaging modalities include a mydriatic imaging mode and a non-mydriatic imaging mode.

7. The method of claim 1, wherein the ophthalmic imaging system includes a fixation light that conveys a fixation direction to a patient, and the GUI includes a blink icon associated with the fixation light, the method further comprising;
    in response to user selection of the blink icon, causing the fixation light to strobe.

8. The method of claim 1, wherein:
the information-display region displays ophthalmic information;
the GUI includes a laterality icon that specifies whether the ophthalmic information displayed in the information-display region is from a left eye or right eye of a patient, and indicates whether the specified laterality is from the patient's point of view or from a doctor's point of view; and
user selection of the laterality icon toggles the laterality between the doctor's and the patient's point of view.

9. The method of claim 1, further comprising:
in response to the ophthalmic imaging system gaining access to a computer network, announcing its presence to other computing systems on the computer network, automatically identifying at least one other computing system on the network having needed patient records and retrieving, over the computing network, the needed patient records from the at least one other computing system excluding any images associated with the retrieved needed patient records;
in response to user selection of a target option associated with a retrieved patient record, initiating retrieval of the images associated with the target option irrespective of whether the user has elected to view any image associated with the target option.

10. A method comprising:
displaying a graphical user interface (GUI) on a screen, the GUI including an information-display region that displays a live feed from at least one camera of an ophthalmic imaging system imaging an eye;
overlaying, on the information-display region, an alignment indicator specifying a target view of the eye when in alignment;
wherein the alignment indicator includes at least one of (a) a partially transparent bar indicating a minimum height of the pupil of the eye when aligned, (b) two lines indicating the minimum height of the pupil of the eye when aligned, (c) crosshairs specifying a central location for the eye when aligned, and (d) an oval whose outline specifies a minimum size of the pupil of the eye when aligned; and
wherein the determination of the minimum height or minimum size is based on eye measurements at least partially determined from the live feed.

11. A method comprising:
capturing an image of the eye using a fundus camera;
determining whether the retina of the eye is within the captured imaged, designating the captured image as valid if the retina is determined to be within the captured image, and designating the captured image as not valid if the retina is not determined to be within the captured image;
evaluating an illumination of a predefined number of consecutive valid images; and
adjusting a gain value of the fundus camera based at least in part on the evaluated illumination.

12. The method of claim 11, wherein:
the captured image from fundus camera is a first image; and
the step of determining whether the retina of the eye is within the captured imaged includes:
capturing a second image excluding the fundus using a second camera;
determining the presence of the retina in the first imaged based at least in part on the second image.

13. A method comprising:
displaying a graphical user interface (GUI) on a screen, the GUI including an information-display region;
wherein the GUI includes a privacy icon depicting a computer display with an attached window shade that is at least partly opened, the method further comprising:
in response to a user selection of the privacy icon by an input device, removing from view information currently displayed in the information-display region;
at least partially closing the window shade of the privacy icon in response to the user selection of the privacy icon, the closing of the window shade including a depiction of the window shade moving over the computer display of the privacy icon; and
the removing from view of information in the information-display region includes an overlay that travels over, and covers, the information-display region, the traveling of the overlay mimicking the closing of the window shade.

14. A method comprising:
displaying a graphical user interface (GUI) on a screen, the GUI including a source icon and a destination icon, the method further comprising:
associating at least one source file with the source icon, and associating at least one destination file with the destination icon;
in response to a user input by an input device, copying user-made annotations on the source files associated with the source icon to the destination files associated with the destination icon, wherein:
the at least one source file is a source image file and the at least one destination file is a destination image file;
the user-made annotations on the source image file define an area of the source image file; and
the user-made annotations are copied to a matching area of the destination image file.

15. A method comprising:
displaying a graphical user interface (GUI) on a screen, the GUI including an information-display region, the information-display region displaying a montaged image comprised of at least two fundus images; and
the GUI includes a montage icon depicting the outer perimeter shape of the montaged image, the montage icon being divided into sectors, each sector corresponding to a separate one of the fundus images, and indicating the boundaries of the fundus images in the montaged image.

16. A method comprising:
displaying a graphical user interface (GUI) on a screen, the GUI including an information-display region, wherein the information-display region displays a selection of images, the method further comprising:
in responding to user selection of a target image within the selection of images,
(a) identifying acquisition parameters of the target image including at least one of a fixation angle, imaging mode, laterality, and field-of-view (FOV), patient ID;
(b) accessing an image database and identifying at least one second image having acquisition parameters matching the identified acquisition parameters of the target image; and
(c) displaying the at least one second image.

17. A method comprising:
displaying a graphical user interface (GUI) on a screen, the GUI including an information-display region, wherein the information-display region displays a patient record access portal having a plurality of user-selectable options, at least one user-selectable option being a target option associated with one or more images, the method further comprising:

in response to user selection of the target option, initiating loading of the images associated with the target option irrespective of whether the user has elected to view any image associated with the target option;

for each loaded imaged, creating a plurality of copies of the loaded image, the plurality of copies being of decreasing resolution and being stored in an image cache; and responding to the user electing to view a specific image associated with the target option within a viewport of first resolution by displaying, from the image cache, a lower resolution copy of the specific image whose lower resolution is closest to, but higher than, the first resolution of the viewport.

18. The method of claim 17, wherein the responding to the user electing to view the specific image further includes:

cropping an area of the copy to be displayed, the cropped area corresponding to the viewport; and resizing the cropped area to match the resolution of the viewport, and displaying the resized cropped area in the viewport.

19. The method of claim 17, further comprising:

responding to the viewport specifying a zoom selection by, if the resolution of the currently displayed copy is greater than the zoom selection of the viewport, cropping the currently displayed copy to display the zoom selection without applying a scaling factor to the copy, else replacing the currently displayed copy with another copy whose resolution is closest to, but greater than, the resolution of the zoom selection of the viewport.

20. The method of claim 17, further comprising:

responding to a panning action of the viewport by defining a cropped area of the currently displayed copy, the cropped area being larger than the viewport and the panning action being executing within the cropped area if fully contained within the cropped area, and responding to the panning action coming within a predefined distance from a boarder of the current cropped area by replacing the current cropped area with a new cropped area shifted from the currently cropped area.

* * * * *

UNITED STATES PATENT AND TRADEMARK OFFICE
CERTIFICATE OF CORRECTION

| | | |
|---|---|---|
| PATENT NO. | : 11,412,928 B2 | Page 1 of 1 |
| APPLICATION NO. | : 16/633139 | |
| DATED | : August 16, 2022 | |
| INVENTOR(S) | : Gregory Anderson et al. | |

It is certified that error appears in the above-identified patent and that said Letters Patent is hereby corrected as shown below:

On the Title Page

In item (57), in Column 2, in "Abstract", Line 2, delete "GUI" and insert -- (GUI) --.

On the page 2, in Column 2, under "Other Publications", Line 35, delete "IEE" and insert -- IEEE --.

On the page 2, in Column 2, under "Other Publications", Line 37, delete "datasets,"" and insert -- data sets," --.

On the page 2, in Column 2, under "Other Publications", Line 58, delete "IEE" and insert -- IEEE --.

In the Specification

In Column 3, Line 34, delete "in in" and insert -- in --.

In Column 6, Line 51, delete "system" and insert -- system. --.

In Column 7, Line 27, delete "reference)." and insert -- reference. --.

In Column 27, Line 5, delete "23c" and insert -- 23e --.

In Column 31, Line 47, delete "Enhanced" and insert -- Extended --.

Signed and Sealed this
Tenth Day of January, 2023

*Katherine Kelly Vidal*

Katherine Kelly Vidal
*Director of the United States Patent and Trademark Office*